(12) United States Patent
Gantier et al.

(10) Patent No.: US 8,318,924 B2
(45) Date of Patent: Nov. 27, 2012

(54) IMMUNOSTIMULATORY SIRNA MOLECULES

(76) Inventors: Michael Paul Marie Gantier, Clayton Vic (AU); Stephen Tong, Clayton Vic (AU); Bryan Raymond George Williams, Clayton Vic (AU)

(*) Notice: Subject to any disclaimer, the term of this patent is extended or adjusted under 35 U.S.C. 154(b) by 0 days.

(21) Appl. No.: 12/867,656

(22) PCT Filed: Feb. 16, 2009

(86) PCT No.: PCT/AU2009/000175
§ 371 (c)(1),
(2), (4) Date: Nov. 2, 2010

(87) PCT Pub. No.: WO2009/100502
PCT Pub. Date: Aug. 20, 2009

(65) Prior Publication Data
US 2011/0039915 A1    Feb. 17, 2011

(30) Foreign Application Priority Data

Feb. 14, 2008    (AU) ............................... 2008900689

(51) Int. Cl.
*C07H 21/04*    (2006.01)
(52) U.S. Cl. .................... 536/24.5; 536/24.31; 536/24.1; 435/6; 435/325; 435/375; 514/44

(58) Field of Classification Search ........................ None
See application file for complete search history.

(56) References Cited

U.S. PATENT DOCUMENTS 7,723,510 B1 * 5/2010 Tuschl et al. ................. 536/24.5
2007/0111228 A1 * 5/2007 Jayasena et al. ................. 435/6

OTHER PUBLICATIONS

McManus et al. RNA 2002, vol. 8:842-850.*
Rose et al. Nucleic Acids Research 2005, vol. 33:4140-4156).*

* cited by examiner

*Primary Examiner* — Kimberly Chong
(74) *Attorney, Agent, or Firm* — Knobbe Martens Olson & Bear LLP

(57) ABSTRACT

The present invention relates to a double-stranded siRNA molecule that is capable of silencing gene expression as well as inducing an immune response. The molecule comprises a sense strand and an antisense strand, wherein the antisense strand comprises a first nucleotide sequence that is specifically complementary to mRNA transcribed from a target gene, and the sense strand comprises a second nucleotide sequence that is substantially or perfectly complementary to the antisense strand with the exception that the second nucleotide sequence comprises at least one immunostimulatory motif comprising two or more non-complementary nucleotides. Such a molecule may be utilized in a method of treating or preventing a disease or condition (such as a viral infection, a bacterial infection, or cancer) in a subject.

14 Claims, 13 Drawing Sheets

Figure 1

LAM-N

| | | | | |
|---|---|---|---|---|
| | LAM-NS | 5' | GAAGGAGGGUGACCUGAUAGCUGCU | SEQ ID NO: 1 |
| | LAM-NAS | 3' | UUCUUCCUCCCACUGGACUAUCGACGA | SEQ ID NO: 2 |

LAM-1

| | | | | |
|---|---|---|---|---|
| | LAM-1S | 5' | GAAGGAGGGUGACCUGAUA`AACCAA` | SEQ ID NO: 3 |
| | LAM-1AS | 3' | UUCUUCCUCCCACUGGACUAU`UUGGUU` | SEQ ID NO: 4 |

LAM-3

| | | | | |
|---|---|---|---|---|
| | LAM-3S | 5' | GAAGGAGGGUGACCUGAUA::::`GGUU`AC | SEQ ID NO: 5 |
| | LAM-3AS | 3' | UUCUUCCUCCCACUGGACUAU`UUGGUG` | SEQ ID NO: 6 |

LAM-4

| | | | | |
|---|---|---|---|---|
| | LAM-4S | 5' | GAAGGAGG `U` `UU` CCUGAUAGCUGCU | SEQ ID NO: 7 |
| | LAM-NAS | 3' | UUCUUCCUCCCACUGGACUAUCGACGA | SEQ ID NO: 2 |

Figure 2

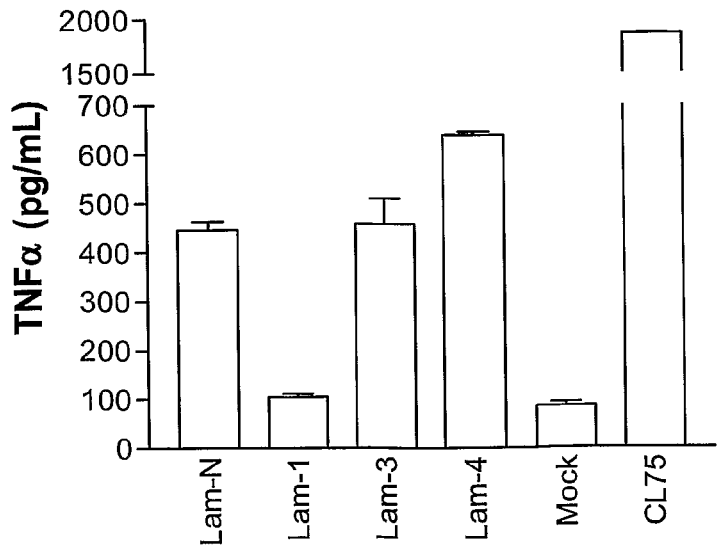

Figure 8
A
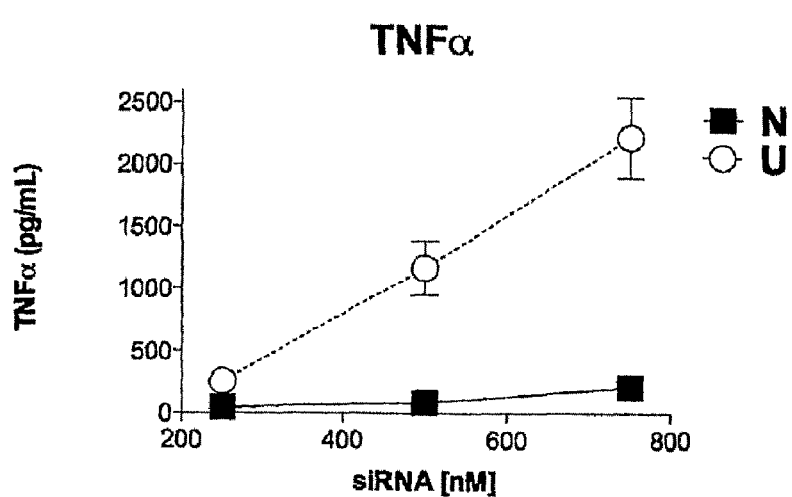
B
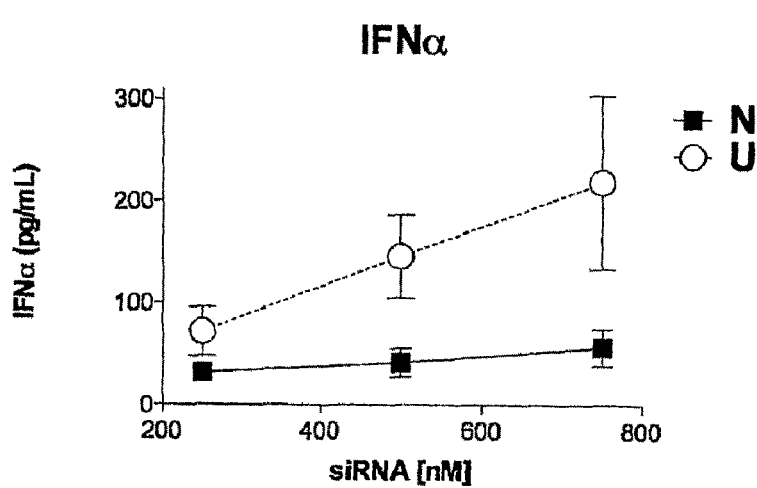

Figure 9

```
Lam-N
LAM-N-S      5'    GAAGGAGGGUGACCUGAUAGCUGCU 3'    SEQ ID NO: 1
LAM-N-AS     3'    UUCUUCCUCCCACUGGACUAUCGACGA 5'   SEQ ID NO: 2

Lam-4                       U  UU
LAM-4-S      5'    GAAGGAGG U  CCUGAUAGCUGCU 3'    SEQ ID NO: 7
LAM-N-AS     3'    UUCUUCCUCCCACUGGACUAUCGACGA 5'   SEQ ID NO: 2

EGFP-N
EGFP-N-S     5'    GCGCCGAGGUGAAGUUCGAGGGCGA 3'    SEQ ID NO: 12
EGFP-AS      3'    GGCGCGGCUCCACUUCAAGCUCCCGCU 5'   SEQ ID NO: 13

EGFP-U                      U  UU
EGFP-U-S     5'    GCGCCGAG U  AGUUCGAGGGCGA 3'    SEQ ID NO: 14
EGFP-AS      3'    GGCGCGGCUCCACUUCAAGCUCCCGCU 5'   SEQ ID NO: 13

E7-N
E7-N-S       5'    ACCGGACAGAGCCCAUUACAAUAUU 3'    SEQ ID NO: 18
E7-AS        3'    CUUGGCCUGUCUCGGGUAAUGUUAUAA 5'   SEQ ID NO: 19

E7-U                        UUUU
E7-U-S       5'    ACCGGACA     CCAUUACAAUAUU 3'    SEQ ID NO: 20
E7-AS        3'    CUUGGCCUGUCUCGGGUAAUGUUAUAA 5'   SEQ ID NO: 19

β-Gal-N
B-Gal-N-S    5'    UUAUGCCGAUCGCGUCACAUU 3'        SEQ ID NO: 15
B-Gal-AS     3'    TTAAUACGGCUAGCGCAGUGU    5'     SEQ ID NO: 16

B-Gal-U                     U  UU
B-Gal-U-S    5'    UUAUGCCG U  CGUCACAUU 3'        SEQ ID NO: 17
B-Gal-AS     3'    TTAAUACGGCUAGCGCAGUGU    5'     SEQ ID NO: 16
```

IMMUNOSTIMULATORY SIRNA MOLECULES

RELATED APPLICATIONS

This application is a U.S. National Phase of International Application No.: PCT/2009/000175, filed Feb. 16, 2009, designating the U.S. and published in English on Aug. 20, 2009 as WO 2009/100502 A1, which claims the benefit of Australian Application No. 2008900689, filed Feb. 14, 2008.

FIELD OF THE INVENTION

The present invention relates to a double-stranded siRNA molecule that is capable of silencing gene expression as well as inducing an immune response. Such a molecule may be utilised in a method of treating or preventing a disease or condition (such as cancer, a viral infection, bacterial infection) in a subject.

INCORPORATION BY REFERENCE

The present application claims priority from:
AU2008900689 titled "IMMUNOSTIMULATORY MOLECULES" and filed on 14 Feb. 2008. The entire content of this application is hereby incorporated by reference.

The following patent specifications are referred to in the following description:
EP1764108 titled "Compositions comprising immunostimulatory RNA oligonucleotides and methods for producing said RNA oligonucleotides"; and
U.S. Pat. No. 6,989,442 titled "Deprotection and purification of oligonucleotides and their derivatives".

The entire content of these specifications is also hereby incorporated by reference.

BACKGROUND OF THE INVENTION

RNA interference (RNAi) is a mechanism of inhibiting the expression of a specific gene (ie gene silencing), wherein double-stranded RNA molecules induce sequence-specific degradation of the mRNA transcripts of a given gene, thereby inhibiting translation of the mRNA into protein. The RNAi pathway is conserved within plants and mammalian cells (Fire et al., 1998) and is thought to be important for inhibiting viral replication, regulating development, and maintenance of the genome.

Is thought that when exogenous double-stranded RNA (eg a virus with an RNA genome) is encountered by a cell, the RNA is imported into the cytoplasm and cleaved into short fragments by an enzyme termed Dicer. These short fragments are 21- to 25-nucleotide, double-stranded small interfering RNA (siRNA) molecules with 2-nucleotide overhangs at the 3' ends. The siRNA molecules are then believed to be incorporated into a complex termed the RNA-induced silencing complex (RISC; Hannon and Rossi, 2004). Here, the two strands of the siRNA molecule are separated, with one strand (the guide strand) retained by the complex, while the remaining strand (the passenger strand) is degraded. Either strand can be the guide strand, and factors such as the thermodynamic stability of the 5' ends of the duplexes can enhance the likelihood of a given strand being selected as the guide strand (Khvorova et al., 2003). The guide strand actively "guides" the activated RISC to complementary (sense) mRNA sequences, triggering cleavage of the mRNA sequence by an Argonaute protein (Diederichs and Haber, 2007), which ultimately prevents or reduces translation of the mRNA into protein, thereby "silencing" or "knocking down" gene expression. siRNA molecules are generally considered to be perfectly complementary; that is, they perfectly base-pair bind to their complementary nucleotide sequence following Watson-Crick base pairing for RNA sequences, such that adenine (A) bases pair with uracil (U) bases, and cytosine (C) bases pair with guanine (G) bases.

Synthetically synthesised siRNA molecules introduced into cells can enter this RNAi pathway and have become an important research tool for knocking down the expression of a specific gene of interest in the laboratory to investigate its function. Such molecules also offer considerable promise for treating diseases associated with the inappropriate expression (eg over-expression) of a particular protein.

During attempts to develop techniques to efficiently deliver synthetic siRNA molecules and artificially trigger RNAi in vivo, it has been noted that siRNA molecules could activate cells of the immune system and induce the production of cytokines both in vivo and in vitro (Sledz et al., 2003; Marques and Williams, 2005; Sioud and Sorensen, 2003; Kariko et al., 2004). Generally, this immunostimulatory effect of siRNA has been regarded as a deleterious, non-specific side-effect that reduces the potential of RNAi to be used both in the laboratory and in the clinic, and substantial research has therefore been undertaken to understand and reduce immunostimulation associated with artificial triggering of RNAi.

In this regard, it has been found that double-stranded RNA molecules stimulate the human innate immune response through toll-like receptor (TLR) 7 and TLR8 in a sequence dependent manner. The relative functional importance of TLR7 and TLR8 is unclear because TLR7 is functional in both humans and mice, whilst TLR8 is functional only in humans (Heil et al., 2004). The binding of ligands to human TLR7 has been shown to stimulate mainly interferon (IFN)-$\alpha$ responses in plasmacytoid dendritic cells (pDC; Hemmi et al., 2002; Jurk et al., 2002), whilst the binding of ligands to human TLR8 has been shown to induce production of proinflammatory cytokines, notably tumour necrosis factor (TNF)-$\alpha$, in activated monocytes (Gorden et al., 2005; Jurk et al., 2006). It has also been shown that IFN$\alpha$ induction may be more specific to human TLR7 signalling and that TNF$\alpha$ induction may reflect more of a human TLR8 response (Gorden et al., 2005).

Further, it has been shown that the size of siRNA molecules may play a role in immunostimulation, as shorter siRNA molecules have been shown to be poor inducers of IFN$\alpha$ expression in pDCs (Hornung et al., 2005). Moreover, guanine- and uridine-rich sequences seem to be preferentially recognised by the innate immune response system (Heil at al., 2004; Diebold et al. 2004), and "GU" motifs may be involved (Heil et al., 2004); however, some siRNA molecules are, notably, not immunostimulatory despite being guanine- and uridine-rich (Sioud, 2005), and it remains unclear if immunostimulatory motifs are recognised in the context of double-stranded RNA (Marques and Williams, 2005). It is, accordingly, possible that the position of the guanylate and uridylate nucleotides within an siRNA molecule, particular motifs (such as GU motifs) or the proportion of guanylate and uridylate nucleotides may play a role in the nature of the cytokine response induced. However, while many researchers have investigated using siRNA sequences with a low guanylate and uridylate content in order to avoid stimulating an innate immune response, it has been found that it is not always possible to pick a suitable sequence for siRNA molecules (ie one that is low in guanylate and uridylate nucleotides) that still efficiently silences gene expression.

The present applicant has realised that the activation of the innate immune response system when silencing the expression of genes in certain scenarios (eg when treating viral infections and cancerous tumours) is desirable as it may actually enhance the therapeutic effect of treatment, as immunostimulation may enhance anti-viral or anti-tumour immune responses. Further, the present applicant has designed a modification that may be potentially made to any double-stranded siRNA molecule, which enhances or confers immunostimulatory activity while maintaining a desired gene silencing effect.

SUMMARY OF THE INVENTION

In a first aspect, the present invention provides an isolated or synthesised double-stranded siRNA molecule comprising a sense strand and an antisense strand, wherein the antisense strand comprises a first nucleotide sequence that is specifically complementary to mRNA transcribed from a target gene, and the sense strand comprises a second nucleotide sequence that is substantially or perfectly complementary to the antisense strand with the exception that the second nucleotide sequence comprises at least one immunostimulatory motif comprising two or more non-complementary nucleotides.

The at least one immunostimulatory motif comprising two or more non-complementary nucleotides (ie non-complementary to the antisense strand) may comprise non-complementary nucleotides representing "mismatches" to a corresponding nucleotide on the antisense strand, thereby forming one or more "bulge" in the secondary structure of the sense strand when hybridised to the antisense strand. Preferably, the at least one immunostimulatory motif comprises a polyuridine motif (eg UUU, UUUU, UUUUUU etc).

The siRNA molecule of the present invention possesses immunostimulatory activity while maintaining effective gene silencing activity.

Therefore, in a second aspect, the present invention provides a method of immunostimulating a cell comprising contacting said cell with the siRNA molecule of the first aspect.

In a third aspect, the present invention provides a method of silencing the expression of a target gene in a cell comprising introducing the siRNA molecule of the first aspect into the said cell.

In a fourth aspect, the present invention provides a method of simultaneously immunostimulating a cell of a subject and silencing the expression of a target gene in the same or another cell of said subject, said method comprising administering to the subject the siRNA molecule of the first aspect.

In a fifth aspect, the present invention provides an expression cassette or vector for transcription of an intermediate RNA molecule capable of being processed by a cell into an siRNA molecule according to the first aspect.

In a sixth aspect, the present invention therefore provides a composition for introducing an siRNA molecule into a cell, said composition comprising an siRNA molecule of the first aspect or an expression cassette or vector of the fifth aspect, optionally in combination with a pharmaceutically- or veterinary-acceptable carrier.

The present invention also extends to a method of treating or preventing a disease or condition (such as a viral infection or cancer) in a subject, said method comprising administering to said subject an effective amount of an siRNA molecule of the first aspect or the composition of the sixth aspect.

BRIEF DESCRIPTION OF THE FIGURES

FIG. 1 provides the sense (S) and antisense (AS) nucleotide sequences and hybridisation of siRNA molecules (LAM-N, LAM-1, LAM-3, and LAM-4) targeted to the Lamin gene, aligned to show complementary binding of the sequences, with modified nucleotides (compared to the control native sequence of LAM-N) highlighted in grey and with non-complementary (mismatched) nucleotides shown out of alignment following Watson-Crick base pairing;

FIG. 2 provides a graph showing TNFα expression in RAW-ELAM cells following transfection with the Lamin-targeting siRNA molecules;

FIG. 8 provides graphs of (A) TNFα and (B) IFNα levels in cell supernatants from PBMCs transfected with EGFP-targeting native (N) and uridine bulge-containing (U) siRNA molecules;

FIG. 9 provides the sense (S) and antisense (AS) nucleotide sequences and hybridisation of siRNA molecules (LAM-N and LAM-4, EGFP-N and EGFP-U, E7-N and E7-U, β-GAL-N and β-GAL-U), aligned to show complementary binding of the sequences, with modified nucleotides in the uridine bulge-containing (U)siRNA molecules (compared to the corresponding control native (N) siRNA molecules) highlighted in grey and with non-complementary (mismatched) nucleotides shown out of alignment following Watson-Crick base pairing;

DETAILED DESCRIPTION OF THE INVENTION

Figure 3:
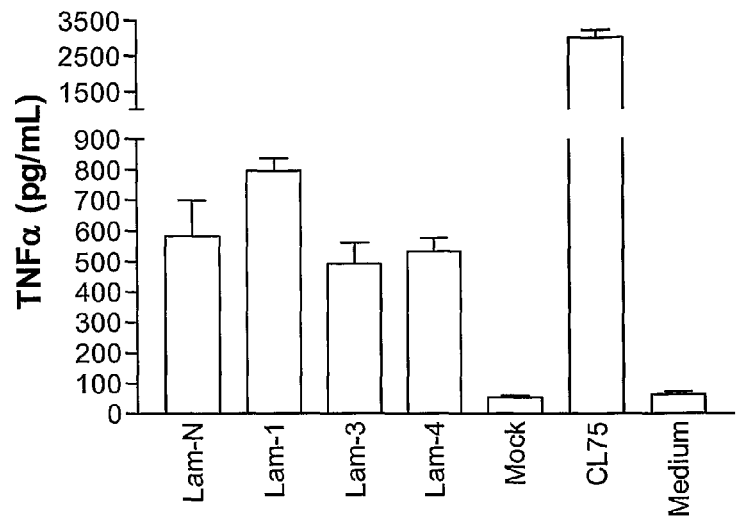
FIG. 3 provides a graph showing TNFα, expression in THP-1 cells following transfection with the Lamin-targeting siRNA molecules.

The present applicant has identified a sequence modification that may be made to potentially any double-stranded siRNA molecule of interest that enhances or confers immunostimulatory activity without substantial loss of the desired gene silencing effect. To achieve this, a number of double-stranded siRNA molecules were designed based on the native sequence of a target gene, each with a modification containing a guanine- and/or uridine-rich motif. The siRNA molecules were tested for their ability to stimulate cytokine responses through TLR7 and TLR8 signalling pathways, as well as their ability to silence expression of the gene of interest. It was surprisingly found that the introduction of the modification into the siRNA molecules efficiently enhanced immunostimulation relative to an unmodified, control siRNA (ie based upon a native sequence of the target gene) and maintained effective gene silencing.

Accordingly, in a first aspect, the present invention provides an isolated or synthesised double-stranded siRNA molecule comprising a sense strand and an antisense strand, wherein the antisense strand comprises a first nucleotide sequence that is specifically complementary to mRNA transcribed from a target gene, and the sense strand comprises a second nucleotide sequence that is substantially or perfectly complementary to the antisense strand with the exception that the second nucleotide sequence comprises at least one immunostimulatory motif comprising two or more non-complementary nucleotides.

The term "siRNA" will be readily understood by persons skilled in the art to refer to a short interfering RNA oligonucleotide molecule, which is usually double-stranded and between 10 and 40 nucleotides in length, and is capable of entering the RNAi pathway to inhibit the expression of a specific gene in a sequence dependent manner.

The term "sense strand" is to be understood as referring to the oligonucleotide strand of a double-stranded DNA or RNA oligonucleotide molecule that is generally considered to code for amino acids, and from which proteins may be translated (although regions of the sense strand may be untranslated or untranscribed). Messenger RNA (mRNA), which will be well known to persons skilled in the art, is considered to be sense strand RNA. The term "antisense strand" is to be understood as referring to the other strand of a double-stranded DNA or RNA oligonucleotide molecule, which is not generally considered to code for amino acids or proteins (ie the "nonsense strand"; although there may be some rare circumstances where the antisense strand does, in fact, code for amino acids or proteins). Both of these terms will be readily understood by persons skilled in the art.

As used herein, the term "complementary" is to be understood to describe the relationship between two strands of a double-stranded DNA or RNA oligonucleotide molecule, wherein the two strands hybridise to each other via the well-known Watson-Crick base-pairing bonds, such that adenine (A) bases pair with uracil (U) bases in RNA strands or thymine (T) bases in DNA strands; and cytosine (C) bases pair with guanine (G) bases in both RNA and DNA strands.

In the context of the antisense strand of the siRNA molecule of the present invention, the nucleotide sequence is described herein as being "specifically complementary to mRNA transcribed from a target gene", and this is to be understood as meaning that the first nucleotide sequence is sufficiently complementary to the sequence of that mRNA so as to ensure specific gene silencing in a target cell. Generally, this will require that the nucleotide sequence of the antisense strand be highly, or preferably, perfectly (ie 100%), complementary to the mRNA transcribed from the target gene, as would be understood by persons skilled in the art.

On the other hand, in the context of the sense strand of the siRNA molecule of the present invention, the nucleotide sequence is described herein as being "substantially or perfectly complementary to the antisense strand", and this is to be understood as meaning that with the exception of the portion of the second nucleotide sequence comprising the at least one immunostimulatory motif comprising two or more non-complementary nucleotides, the second nucleotide sequence may be perfectly complementary to the antisense strand or otherwise sufficiently complementary so as to allow hybridisation with the antisense strand and permit recognition and cleavage in the RNAi pathway (eg by Dicer).

The term "immunostimulatory motif", as used herein, is to be understood as referring to a short nucleotide sequence, located within an oligonucleotide molecule, wherein the short nucleotide sequence is associated with immunostimulation (ie immune response stimulation). The term therefore includes guanylate- and uridylate-rich sequences (Sioud, 2005), and sequences containing GU motifs (Heil et al., 2004).

In an siRNA molecule according to the present invention, at least one immunostimulatory motif comprising two or more non-complementary nucleotides (ie non-complementary to the antisense strand) is present. The non-complementary nucleotides may represent "mismatches" to a corresponding nucleotide on the antisense strand and/or may represent an insertion of nucleotide(s) (into the sense strand) which has effectively no corresponding nucleotide(s) on the antisense strand. In any case, the non-complementary nucleotides preferably form one or more "bulge" (eg a small loop) in the secondary structure of the sense strand when hybridised to the antisense strand.

Preferably, the at least one immunostimulatory motif comprising two or more non-complementary nucleotides comprises about 2-15 non-complementary nucleotides, more preferably about 2-8 non-complementary nucleotides, and even more preferably, about 3-5 non-complementary nucleotides. In a preferred embodiment, the at least one immunostimulatory motif comprising two or more non-complementary nucleotides comprises three non-complementary nucleotides, and in another preferred embodiment, the at least one immunostimulatory motif comprising two or more non-complementary nucleotides comprises four non-complementary nucleotides. The non-complementary nucleotides are preferably contiguous, however they may be "interrupted" or separated by one or more nucleotides that is/are complementary to a corresponding nucleotide(s) in the antisense strand.

The at least one immunostimulatory motif comprising two or more non-complementary nucleotides may be located anywhere within the nucleotide sequence of the siRNA molecule. However, preferably, the immunostimulatory motif is located at least one nucleotide away from a terminus of the siRNA molecule and, more preferably, at least four nucleotides away from a terminus of the siRNA molecule. Most preferably, the immunostimulatory motif is located at approximately the centre of the siRNA molecule.

Preferably, the at least one immunostimulatory motif comprises a polyuridine motif.

As used herein, the term "polyuridine motif" is to be understood as referring to a short nucleotide sequence consisting entirely of uridylate nucleotides (eg UUU, UUUU, UUU-UUU etc). In accordance with the present invention, two or more of the uridylate nucleotides in such a polyuridine motif preferably represent non-complementary nucleotides (ie non-complementary to the antisense strand). Accordingly, a preferred polyuridine motif may comprise some uridylate nucleotides that are complementary to the antisense strand, but will, essentially, comprise two or more uridylate nucleotides that are non-complementary to the antisense strand. The polyuridine motif may form one or more bulge in the secondary structure of the sense strand when hybridised to the antisense strand of the siRNA molecule.

In addition to the at least one immunostimulatory motif comprising two or more non-complementary nucleotides, an siRNA molecule according to the present invention may comprise one or more additional types of immunostimulatory motif (eg a guanine- and uridine-rich sequence, and/or contain GU motifs such as GGUU, UUGGUG, UUGGUU, UGUGU and GUCCUUCAA). Such additional immunostimulatory motifs may be incorporated into an siRNA molecule by selection of an appropriate target region within the target gene (eg a region on the sense strand of the gene which is guanine- and uridine-rich). Methods and algorithms for predicting immunostimulatory activity of siRNA molecules based upon native gene sequences have been described in EP 1764108, the disclosure of which is to be regarded as incorporated herein by reference.

An siRNA molecule according to the present invention may have one of a variety of different structures. In some embodiments, both ends of the siRNA molecule may be blunt ended. Alternatively, both ends of the siRNA molecule may have a 3' overhang, for example, both ends of the siRNA molecule may have a "symmetric" 3' two-nucleotide overhang. Further, in some embodiments, one end of the siRNA molecule may comprise a blunt end, whilst the other end has an overhang. An overhang may be one nucleotide in length, two nucleotides in length, three nucleotides in length, and so on. For example, it may be preferable that the siRNA molecule comprises a blunt end at the 5' terminus of the antisense strand and a two-nucleotide overhang at the 3' end of the antisense strand. Such molecules are referred to as having an "asymmetric" 3' two-nucleotide overhang.

The length of siRNA molecules that are blunt ended at both ends is described as being the length of the double-stranded molecule. For example, if both strands are 25 nucleotides long, the siRNA molecule is described as being 25 nucleotides long. The length of siRNA molecules that have symmetric 3' two-nucleotide overhangs is described as being the length of the double-stranded molecule "+2". For example, if both strands are 27 nucleotides long, but the portion of the molecule that is double-stranded is 25 nucleotides long and both strands have a 3' two-nucleotide overhang, the siRNA molecule is described as being 25+2 nucleotides long. Similarly, the length of siRNA molecules that have an asymmetric 3' two-nucleotide overhang is described as being the length of the double-stranded molecule "+0/+2". For example, if the sense strand is 25 nucleotides long and the antisense strand is 27 nucleotides long (such that the portion of the molecule that is double-stranded is 25 nucleotides long) the molecule would be described as being 25+0/+2 nucleotides long.

Although siRNA molecules of the present invention comprise two or more non-complementary nucleotides within the portion of the siRNA molecule that is double-stranded, it is to be understood that the same nomenclature applies when describing the length of siRNA molecules of the present invention. For example, if an siRNA molecule of the present invention has a sense strand that is 25 nucleotides long and an antisense strand that is 27 nucleotides long (such that the portion of the molecule that is double-stranded is 25 nucleotides long, including the two or more non-complementary nucleotides positioned within that double-stranded portion) the molecule is still described as being 25+0/+2 nucleotides long. Asymmetric 25+0/+2 siRNA molecules are also described as being "Dicer substrates" and have been shown to exert stronger gene silencing efficiency than shorter symmetric siRNAs (Kim et al., 2005; Rose et al., 2005).

In some embodiments of the present invention, the antisense and/or sense strand of the siRNA molecule is between 19 and 34 nucleotides in length. In some embodiments, the siRNA molecule is between 19+2 and 32+2 nucleotides in length. Preferably, the siRNA molecule of the present invention is between 19+0/+2 and 32+0/+2 nucleotides in length. More preferably, the siRNA molecule is 25+0/+2 nucleotides in length.

An siRNA molecule according to the present invention may be produced by a variety of mechanisms such as those well known to persons skilled in the art, including chemical synthesis (eg solid-phase synthesis as described, for example, in U.S. Pat. No. 6,989,442), in vitro transcription (eg T7, T3 and/or SP6 RNA polymerase transcription with or without processing by ribonucleases such as T1 ribonuclease, or processing by phosphatases), or recombinant human Dicer/*E. coli* RNaseIII digestion of long double-stranded RNA molecules.

The stability of an siRNA molecule according to the present invention may be altered by various means such as chemical modification. For example, the introduction of a phosphorothioate (P=S) backbone linkage at the 3'-end protects against exonuclease degradation, while 2'-sugar modification (such as 2'-O-methyl or 2'-fluoro) provides endonuclease resistance (Layzer et al., 2004; Choung at al., 2006; Allerson et al., 2005; de Fougerolles et al., 2005). Other suitable modifications include the use of 2-thiouridine, pseudouridine, and dihydrouridine modifications (Sipa et al., 2007), and cholesterol/amino-groups conjugation (Kubo et al., 2008).

Due to the high level of complementarity between the first and second nucleotide sequences, persons skilled in the art will appreciate that the antisense and sense strands may be hybridised to one another to form a double-stranded siRNA molecule according to the invention. The hybridisation may occur using any of the methods well known to persons skilled in the art. For example, the hybridisation may involve combining the two single-stranded RNA molecules (ie the antisense and sense strands) together and incubating at a high temperature (ie at or above their "melting" temperature such as, for example, 80 to 98° C.), which allows the molecules to disassociate (or "denature") from one another, and then decreasing the temperature in order for single-stranded RNA molecules with complementary sequences to base-pair bind (ie anneal). This decreased temperature can be at a temperature between room temperature and approximately 65° C., providing that the two single-stranded RNA molecules are able to anneal with one another to produce an siRNA molecule of the present invention Annealing reactions may be performed in any suitable buffer, such as 100 mM potassium acetate with 30 mM HEPES pH7.5 in RNase/DNase-free water.

An siRNA molecule according to the present invention possesses immunostimulatory activity while maintaining effective gene silencing activity. The term "gene silencing" is intended to refer to a reduction in gene expression due to RNAi, that is, due to the sequence-specific degradation of the mRNA transcripts of a specific gene. Gene silencing may lead to the reduction in the specific mRNA transcript, which in turn may lead to a reduction in the level of protein that is translated from the specific mRNA transcripts. Gene silencing may be measured by any of the suitable methods well known to persons skilled in the art such as, for example, any type of quantitative or semi-quantitative SDS-PAGE, Western blot, ELISA, functional assays for the specific protein, real-time PCR, fluorescent activated cell sorting, etc. Persons skilled in the art will understand that the terms "silencing" and "knocking down" can be used interchangeably and may refer to a reduction, rather than a complete elimination, of gene expression.

The gene silencing activity conferred by the siRNA molecule may occur in a targeted cell.

In some embodiments, the immunostimulation conferred by the siRNA molecule may involve the recruitment or upregulation of immune cells such as pDCs, macrophages, B cells, myeloid dendritic cells, natural killer (NK) cells, etc. Further, in some embodiments, the immunostimulation may involve induction of cytokine or other responses due to signalling through receptors such as TLR7 and/or TLR8, or through alternative pathways such as the RIG-I pathway, or by other means. Moreover, in some embodiments, the immunostimulation (eg due to TLR7 and/or TLR8 signalling, RIG-I signalling or other signalling pathways) may occur in cells other than the cell targeted for gene silencing activity. Accordingly, immunostimulation may be measured using any of the suitable methods well known to persons skilled in the art. For example, immunostimulation may be measured by detecting an increase in recruitment of immune cells such as pDCs and macrophages, but may also include other immune cells such as B cells, myeloid dendritic cells, natural killer (NK) cells, etc. Alternatively, immunostimulation may be measured by detecting an increase in cytokines or other immune system signalling molecules, for example, increases in cytokines such as TNFα, IFNα, IFNβ, IFNγ, IL-1β, IL-2, IL-4, IL-5, IL-6, IL-7, IL-8, IL-10, IL-12, IL-15, IL-17, G-CSF, GM-CSFRANTES, Cxcl10, MIP-1β, or MCP, etc. As double-stranded RNA molecules are understood to stimulate the human innate immune response through binding with TLR7 and/or TLR8, and TLR7 and TLR8 signalling are associated with, predominately, increases in IFNα and TNFα, respectively, IFNα and TNFα are useful in detecting immunostimulation following contact of the siRNA molecule with a cell.

In some embodiments, the siRNA molecules of the present invention may be derived from corresponding "native" siRNA molecules (ie by the inclusion of the at least one immunostimulatory motif comprising two or more non-complementary nucleotides), which have low immunostimulatory activity.

The present applicant has realised that, in some circumstances, immunostimulation during gene silencing may be beneficial (eg for treating viral infections or cancers).

Therefore, in a second aspect, the present invention provides a method of immunostimulating a cell comprising contacting said cell with the siRNA molecule of the first aspect.

The siRNA molecule may be contacted with the cell using any of the suitable methods well known to persons skilled in the art. For example, the siRNA molecule may be simply admixed with the cell, where it may contact cell surface receptors and may be taken into the cell via a variety of means such as endocytosis or receptor-mediated uptake as either naked siRNA molecules or following formulation with various transfection reagents, liposomes, cationic liposomes, stable nucleic acid lipid particles, nanoparticles with or without charged particles but particularly with positively-charged particles, polymers such as polyethylenimine, bacterial mini-cells (MacDiarmid et al., 2007) or other delivery vehicles. Alternatively, the siRNA molecule may be actively introduced into cells via methods such as electroporation, or transfected into cells in culture using standard protocols and reagents (eg such as lipofectamine, DOTAP™ transfection reagent, or delivered to cells using other nucleotide delivery methods such as vectors (eg viral vectors such as adenoviruses or retroviruses encoding short hairpin RNA (shRNA)) or plasmid vectors encoding shRNA such as small hairpin expression vectors), or via gene therapy techniques, etc.

Immunostimulation of a cell through contact with an siRNA molecule according to the present invention may be measured in a variety of ways, including those described above in relation to the first aspect of the invention.

In a third aspect, the present invention provides a method of silencing the expression of a target gene in a cell comprising introducing the siRNA molecule of the first aspect into the said cell.

In a fourth aspect, the present invention provides a method of simultaneously immunostimulating a cell of a subject and silencing the expression of a target gene in the same or another cell of said subject, said method comprising administering to the subject the siRNA molecule of the first aspect.

An siRNA molecule according to the present invention may be introduced into a cell by any of the methods well known to persons skilled in the art including by transfection, endocytosis, electroporation, or receptor-mediated uptake as either naked siRNA molecules or following formulation of the siRNA molecules with various transfection reagents, liposomes, cationic liposomes, stable nucleic acid lipid particles, nanoparticles with or without charged particles but particularly with positively charged particles, polymers such as polyethylenimine, bacterial mini-cells (MacDiarmid et al., 2007) or other delivery vehicles as mentioned above.

An siRNA molecule can be delivered systemically or locally, including direct injection into organs or tumours, as well as, for example, via ocular delivery, respiratory delivery, nasal delivery, central nervous system delivery, intracranial delivery, peritoneal delivery, subcutaneaous delivery, vaginal delivery, and rectal delivery.

An siRNA molecule may be expressed in situ (ie within the cell) from an appropriate DNA expression cassette or vector using a technique known as DNA-directed RNAi (ddRNAi). Essentially, the expression cassette or vector (eg viral vector or plasmid vector) comprises a promoter operably linked to DNA encoding an RNA molecule, for example, in the form of an shRNA. The promoter may be such that it enables transcription of the RNA by RNA polymerase III (eg the U6 or HI promoter), or RNA polymerase II using pri-micro-RNA-like hairpin cassettes. An shRNA sequence may comprise the 5' to 3' sequence of the sense strand of the siRNA molecule of the invention, followed by a sequence of 4 to 20 nucleotides encoding a short loop, followed by the 5' to 3' sequence of the antisense strand of the siRNA molecule of the invention. The transcribed RNA polynucleotide molecule may automatically form a hairpin structure due to the highly complementary nature of the sense and antisense sequences of the siRNA molecule of the invention. Such shRNA molecules can be considered intermediate RNA molecules that can then be processed into short fragments by the Dicer enzyme into siRNA molecules.

The expression cassette or vector (eg viral vector or plasmid vector) for transcription of an intermediate RNA molecule can be cloned using conventional cloning techniques known to persons skilled in the art, including polymerase chain reaction (PCR)-based cloning methods, as well as the use of annealed complementary oligonucleotides, or primer extension of hairpin templates. These techniques may utilise specialised DNA polymerases such as high fidelity polymerases, Phi29 polymerase (which is thought to be more able to function in the presence of secondary structure of a hairpin template compared to other polymerases) as described in McIntyre and Fanning (2006), the entire content of which is hereby incorporated by reference, etc.

The expression cassette or vector encoding an siRNA molecule according to the present invention may be introduced into a cell by any of the methods well known to persons skilled in the art including by transfection, endocytosis, electroporation or receptor-mediated uptake as either naked siRNA molecules or following formulation of the siRNA molecules with various transfection reagents, liposomes, cationic liposomes, stable nucleic acid lipid particles, nanoparticles with or without charged particles but particularly with positively charged particles, polymers such as polyethylenimine, mini-cells (MacDiarmid et al., 2007) or other delivery vehicles as mentioned above.

Alternatively, the expression cassette or vector (ie viral vector or plasmid vector) encoding an siRNA molecule according to the present invention may be introduced into a cell by viral vectors known to persons skilled in the art, such as retroviral vectors, adenoviral vectors, herpes viruses or other genetically modified viral vectors.

Thus, in a fifth aspect, the present invention provides an expression cassette or vector for transcription of an intermediate RNA molecule capable of being processed by a cell into a double-stranded siRNA molecule comprising a sense strand and an antisense strand, wherein
    the antisense strand comprises a first nucleotide sequence that is specifically complementary to mRNA transcribed from a target gene, and
    the sense strand comprises a second nucleotide sequence that is substantially or perfectly complementary to the antisense strand with the exception that the second nucleotide sequence comprises at least one immunostimulatory motif comprising two or more non-complementary nucleotides.

The expression cassette or vector for transcription of an intermediate RNA molecule may be capable of being processed by a cell to produce a double-stranded siRNA molecule of the first aspect of the invention.

The methods of the second, third and fourth aspects of the present invention may be used within a laboratory setting or they may be used prophylactically or therapeutically in a clinical or veterinary setting.

Thus, in a sixth aspect, the present invention therefore provides a composition for introducing an siRNA molecule into a cell, said composition comprising an siRNA molecule of the first aspect or an expression cassette or vector of the fifth aspect, optionally in combination with a pharmaceutically- or veterinary-acceptable carrier.

The composition may comprise liposomes, cationic liposomes, stable nucleic acid lipid particles, nanoparticles with or without charged particles but particularly with positively charged particles, polymers such as polyethylenimine, viral vectors, or another delivery vehicle as known to persons skilled in the art, for said siRNA molecule or expression cassette or vector.

The present invention also extends to a method of treating or preventing a disease or condition in a subject, said method comprising administering to said subject an effective amount of an siRNA molecule of the first aspect or the composition of the sixth aspect.

The disease or condition to be treated or prevented may be selected from any disease or condition which may benefit from an enhanced immune response in the subject, especially an immune response involving enhanced IFNα, and/or TNFα, both known to exert, particularly, anti-tumoural activity. Accordingly, the disease or condition may be selected from, for example, cancer (eg breast cancer, cervical cancer, prostate cancer, glioma etc.) and diseases and/or conditions caused by an infectious agent such as a bacteria (eg *Mycobacterium tuberculosis, Pseudomonas aeruginosa*) or a virus (eg respiratory syncytial virus (RSV), herpes simplex virus (HSV), hepatitis B virus (HBV), hepatitis C virus (HCV), human immunodeficiency virus (HIV), severe acute respiratory syndrome (SARS)-coronavirus, influenza virus, and human papillomavirus (HPV)).

Some examples of target genes for an siRNA molecule of the first aspect of the invention include genes in tumour cells that have been shown to code for proteins that are associated with tumour growth and survival, such as growth factors and receptors, anti-apoptotic proteins, down stream signal transduction proteins, proteins associated with angiogenesis, and proteins that may be involved with metastasis (eg vascular endothelial growth factor (VEGF), B-cell lymphoma (Bcl)-2, c-Myc, Raf-1, c-Myc oncogenic transcription factor, etc); genes encoding proteins that are associated with viral replication and survival (eg HBV sAg, Influenza virus nucleoprotein or acidic polymerase, HIV gag, pol or env etc); or genes encoding proteins that are associated with bacterial replication and survival.

The subject will generally be a human patient, however the method may also be useful in other animals, particularly mammals, including livestock and stud animals, and companion animals such as dogs and cats.

The composition can be delivered systemically or locally, including direct injection into organs or tumours, as well as, for example, via ocular delivery, respiratory delivery, nasal delivery, central nervous system delivery, intracranial delivery, peritoneal delivery, subcutaneous delivery, vaginal delivery, and rectal delivery.

The invention is hereinafter described by way of the following, non-limiting examples and accompanying figures.

EXAMPLES

Example 1 siRNA Design

Materials and Methods

The siRNA duplexes were synthesised by Integrated DNA Technology (IDT; Coralville, Iowa, USA).

The sense (S) and antisense (AS) nucleotide sequences of the siRNA molecules are shown in Table 1.

TABLE 1

Lamin siRNA molecules

| siRNA duplex | siRNA single-stranded molecule | 5'-3' Sequence | SEQ ID |
|---|---|---|---|
| LAM-N | LAM-N | GAAGGAGGGUGACCUGAUAGCUGCU | SEQ ID NO. 1 |
| LAM-N | LAM-NAS | AGCAGCUAUCAGGUCACCCUCCUUCU | SEQ ID NO. 2 |

TABLE 1-continued

Lamin siRNA molecules

| siRNA duplex | siRNA single-stranded molecule | 5'-3' Sequence | SEQ ID |
|---|---|---|---|
| LAM-1 | LAM-1S | GAAGGAGGGUGACCUGAUA*AA*CCAA | SEQ ID NO. 3 |
| LAM-1 | LAM-1AS | *UUGGUU*UAUCAGGUCACCCUCCUUCU U | SEQ ID NO. 4 |
| LAM-3 | LAM-3S | GAAGGAGGGUGACCUGAUA*GGUUAC* | SEQ ID NO. 5 |
| LAM-3 | LAM-3AS | *GUGGUU*UAUCAGGUCACCCUCCUUCU U | SEQ ID NO. 6 |
| LAM-4 | LAM-4S | GAAGGAGGUUUUCCUGAUAGCUG CU | SEQ ID NO. 7 |
| LAM-4 | LAM-NAS | AGCAGCUAUCAGGUCACCCUCCUUCU U | SEQ ID NO. 2 |

Bold font denotes polyuridine motif; *italicised* font denotes sequence that is different to the corresponding native siRNA (ie LAM-N), underlined font denotes non-complementary sequence

Results and Discussion

The siRNA molecules were designed using IDT Dicer substrate 27 mer design tool to target gene silencing of the LaminA/C gene (Gene ID: 4000), as a suitable assay for Lamin gene expression had previously been established in the present applicant's laboratory. The siRNA molecules were designed to be double-stranded, the sense strands were 25 nucleotides in length, while the antisense strands were 27 nucleotides in length, such that there was a 3' two-nucleotide overhang on the antisense (guide) strand, and a blunt end at the other terminus, as shown in FIG. 1. The structure of such double-stranded siRNA molecules is referred to as being 25+0/+2 nucleotides in length.

The staggered end at the 5' terminus of the double-stranded molecule (ie due to the 3' two-nucleotide overhang on the anti-sense strand) was selected as it is postulated to enhance silencing and orientates Dicer on the molecule (Kim et al., 2005, Rose et al., 2005). The blunt end of the molecule was selected as it is thought to activate the retinoic acid inducible gene I (RIG-I) RNA helicase (Marques et al., 2006), which is involved in double-stranded RNA-induced signalling (Kikuchi et al., 2004) and promote immunostimulation.

A control siRNA (LAM-N) was designed such that the guide (antisense) strand hybridises to the Lamin mRNA without mismatches (ie LAM-N has the native Lamin gene sequence), and accordingly, this siRNA molecule was used to determine base line levels of gene silencing and immunostimulation. siRNA molecules with variations to this sequence (LAM-1, LAM-3, LAM-4) were then designed in an attempt to enhance or confer immunostimulation but maintain the gene silencing ability of the siRNA.

In comparison, the LAM-1 siRNA duplex sequences were based on LAM-N sequences, except that the immunostimulatory motif UUGGUU replaced the 3'-terminal six nucleotides on the antisense (guide) strand, and the complementary sequence AACCAA (ie when read 3' to 5' as shown in FIG. 1) replaced the corresponding six nucleotides on the sense strand, such that a perfectly paired siRNA duplex was expected.

The LAM-3 siRNA duplex sequences were based on LAM-N sequences, except that the immunostimulatory motif UUGGUG replaced the 3'-terminal six nucleotides of the native sequence on the antisense (guide) strand (ie when read 3' to 5' as shown in FIG. 1), and the immunostimulatory motif GGUUAC replaced the corresponding six nucleotides on the sense strand, such that four G·U wobble base-pairs were created. Wobble base pairing has comparable thermodynamic stability to Watson-Crick base pairing but has different structural properties (Varani and McClain, 2000).

The LAM-4 siRNA duplex sequences were based on LAM-N sequences, except that the immunostimulatory motif UUUU replaced four nucleotides of the native sequence near the centre of the molecule on the sense strand, while the native sequence of the corresponding nucleotides on the antisense (guide) strand was retained such that it read CACU (ie when read 3' to 5' as shown in FIG. 1), and accordingly, three of these four nucleotides were mismatched (ie non-complementary according to Watson-Crick base pairing). It was predicted that this mismatch would result in a "uridine bulge".

Example 2

Immunostimulatory Effect of siRNA Molecules on RAW-ELAM Cells

Materials and Methods
siRNA

The double-stranded siRNA molecules used in this example were as described in Example 1. They were synthesised as single-stranded RNA molecules (ssRNAs) by IDT with HPLC purification, and were resuspended into duplex buffer (100 mM potassium acetate, 30 mM HEPES (pH 7.5), in DNase-RNase-free $H_2O$) to a concentration of 160 µM. Identical volumes of complementary ssRNAs were annealed at 92° C. for 2 min and left for 30 min at room temperature, resulting in a 80 µM solution of double-stranded siRNA molecules.

Cell Culture

RAW-ELAM cells, a mouse leukaemic monocyte macrophage cell line stably transfected with an ELAM promoter driving the expression of luciferase (Hume et al., 2001), were obtained from Ashley Mansell (Monash Institute of Medical Research, Clayton, Australia). RAW cells are known to release TNFα in response to sequence-specific siRNA stimulation (Judge et al., 2005; Hornung et al., 2005). The cells were cultured in Dulbecco's Modified Eagle's Medium (DMEM) (11965-092; Invitrogen Life Technologies) complemented with 10% foetal calf serum (FCS) (FBS-500, ICPBio Ltd, Auckland, New Zealand) and 1× antibiotic/antimycotic (15240-062; Invitrogen Life Technologies). The RAW-ELAM cells were then plated to 90% confluency in a 96-well plate in 150 µl of culture medium for 6 hours, followed by transfection with siRNA duplexes as described below. The supernatants were collected for TNFα analysis 16 to 20 h post-transfection.

Transfection of Double-Stranded siRNA Molecules

The double-stranded siRNA molecules were transfected into cells with DOTAP (1811177; Roche). DOTAP (1.87 µg/µl in 80 µM siRNA) was first diluted in 75 µl RPMI 1640 (11875; Invitrogen Life Technologies) for 5 min before mixing with an equal volume of RPMI 1640 containing 5.6 µl of the siRNA. The resulting mix was incubated for 10-30 min and 50 µl was added per well of a 96-well plate, resulting in a final volume of 200 µl with a concentration of 750 nM of siRNA. Each treatment condition was carried out in biological triplicate and the data presented is representative of a least two independent experiments.

Experimental Controls

CL75 (also known as 3M-002), a TLR8 chemical agonist, was obtained from InvivoGen (tlrl-c75; San Diego, Calif., United States of America) and added directly to the cells to a final concentration of 1 µg/ml as a positive control. A mock transfection control was also performed, which controls for the non-specific effect of the transfection reagent, and accordingly contains DOTAP alone (at a similar concentration as other wells), in the absence of any siRNA.

TNFα Detection

Mouse TNFα in transfected cell supernatants was measured using the OptEIA ELISA set 558874 (BD Biosciences, Franklin Lakes, N.J., United States of America) according to the manufacturer's instructions. TMB substrate (T0440; Sigma-Aldrich Corp, St Louis, Mo., United States of America) was used for quantification of TNFα on a Fluostar OPTIMA (BMG Labtech) plate reader. Results are shown with error bars representing the SEM.

Results and Discussion

TLR7 is functional in both humans and mice, whilst TLR8 sensing of RNA is functional only in humans (Heil et al., 2004), and accordingly, the TNFα release observed in RAW-ELAM cells following transfection of the siRNA molecules is thought to be due to signalling via TLR7.

As shown in FIG. 2, LAM-N induced a higher level of TNFα expression than LAM-1, suggesting that the LAM-N is inherently immunostimulatory. Interestingly, the motif UUGGUU (3'-5' on the antisense strand) of LAM-1, when hybridised to its perfectly complementary sequence, in fact, suppressed TNFα expression in comparison with LAM-N. LAM-3 induced a similar level of TNFα expression as LAM-N, suggesting that the motif UUGGUG (3' to 5' on the antisense strand) of LAM-1, when paired with the non-complementary sequence GGUUAC (5' to 3' on the sense strand as shown in FIG. 1), did not, in fact, enhance immunostimulation, whereas in contrast, LAM-4 with the motif UUUU (5' to 3' on the sense strand) induced an increase in TNFα expression in comparison to LAM-N, indicating that the uridine bulge present in LAM-4 is at least as immunostimulatory as the native sequence.

The number of uridylate nucleotides in an siRNA molecule has been suggested to be important for immunostimulation, however LAM-1 has two more uridylate nucleotides in the entire double-stranded RNA molecule than does LAM-N. On the other hand, LAM-1 does have two less uridylate nucleotides on the sense strand than does LAM-N, and TLR7 signalling is markedly attenuated. Further, LAM-4 has three more uridylate nucleotides in the entire double-stranded siRNA molecule, all of which are in the sense strand, and this enhanced TLR7-mediated immunostimulation. This suggests that the number of uridylate nucleotides on the sense strand of a double-stranded RNA molecule, rather than the entire molecule, may be a factor in stimulating signalling via TLR7. Alternatively, the presence of the uridine bulge and the position of the uridylate nucleotides within the sense strand of LAM-4 may be responsible for the increase in TLR7-mediated immunostimulation.

Example 3

Immunostimulatory Effect of siRNA Molecules on THP-1 Cells

Materials and Methods
siRNA

The double-stranded siRNA molecules used in this example were as described in Example 1, annealed as described in Example 2.

Cell Culture

THP-1 cells, a human monocytic cell line which can be activated with PMA/IFNγ to form a macrophage-like cell line, were obtained from Ashley Mansell (Monash Institute of Medical Research, Clayton, Australia). It had been previously demonstrated that IFNγ pre-treated PMA-differentiated THP-1 cells are able to release TNFα, in response to TLR8 and TLR7 stimulation with short RNA in a sequence specific manner (Gantier et al., 2008). Therefore, TNFα production by THP-1 in response to siRNA treatment indicates both TLR7 and TLR8 are recruited. THP-1 cells were maintained in complete RPMI-1640 and subcultured in suspension every 2-3 days until passage (p<25). For experiments, 80,000 THP-1 cells were differentiated for 16 h in conditioned medium with PMA at 20 ng/ml (in DMSO 524400; Calbiochem) per well of a 96-well plate at 37° C. in a 5% $CO_2$ atmosphere. Priming of adherent PMA-treated THP-1 was conducted by rinsing the cells with 150 µl of complete RPMI-1640 supplemented with 100 U/ml human IFNγ (IF002, $ED_{50}$<0.05 ng/ml; Chemicon International) for 6 h at 37° C., 5% $CO_2$. The cells were subsequently rinsed with 100 µl of complete RPMI 1640 before transfection with double-stranded siRNA molecules as described in Example 2, with a final volume of 150 µl at 1 µM of siRNA. Each treatment was carried out in biological triplicate and the data presented is representative of a least two independent experiments. CL75 and mock transfection controls were performed as described in Example 2. Additionally, a medium control was performed wherein cells were untreated (ie in culture medium only).

TNFα Detection

Human TNFα in transfected cell supernatants was measured using the OptEIA ELISA set 555212 (BD Biosciences) according to the manufacturer's instructions. TMB substrate (T0440; Sigma-Aldrich) was used for quantification of TNFα, on a Fluostar OPTIMA (BMG Labtech) plate reader. Results are shown in FIG. 3 with error bars representing SEM.

Results and Discussion

The binding of ligands to human TLR7 and TLR8 has been shown to induce the production of proinflammatory cytokines, notably TNFα, in activated monocytes (Gorden et al., 2005; Jurk et al., 2006). However, TNFα release observed in THP-1 cells following transfection with the siRNA molecules is thought to be mainly due to the recruitment of TLR8, as TLR8 is highly upregulated in IFNγ treated THP-1 cells, although TLR7 was also shown to be involved in RNA sensing in these cells (Gantier et al., 2008).

As shown in FIG. 3, LAM-1 induced a higher level of TNFα expression than LAM-N, whereas LAM-3 and LAM-4 induced a similar level of TNFα as compared to LAM-N. Importantly, both LAM-3 and LAM-4 retained immunostimulation when compared to the mock transfection control. As human TLR8 sensing is associated with the predominant pathway for TNFα release in the THP-1 cell model, the results demonstrate that LAM-3 and LAM-4 trigger human TLR8 signalling.

Thus, the level of immunostimulation induced by LAM-4 (compared to LAM-N) transfection in THP-1 cell model was marginally lower, whereas the level of immunostimulation induced by LAM-4 (compared to LAM-N) was higher in the RAW-ELAM cell model (ie as shown in Example 2). This data indicates that the addition of a uridine bulge in the context of the Lamin siRNA sequence does not have any significant adverse effect on TLR7/8 recruitment, and potentially increases immunostimulation.

Example 4

Immunostimulatory Effect of siRNA Molecules on PBMCs

Materials and Methods
siRNA

The double-stranded siRNA molecules used in this example were as described in Example 1, annealed as described in Example 2.

Cell Culture

Human peripheral blood mononuclear cells (PBMCs) were isolated as follows. Fresh blood from healthy male donors was collected in heparin-treated tubes, and submitted to Ficoll-Paque plus (17-1440-02; GE Healthcare, Chalfont, St Giles, United Kingdom) gradient purification following the manufacturer's guidelines. Isolated cells were then plated in a 96-well plate at $2 \times 10^5$ cells/well in RPMI 1640 plus L-glutamine medium (11875; Invitrogen Life Technologies, Carlsbad, Calif., United States of America) complemented with 1× antibiotic/antimycotic (15204064; Invitrogen Life Technologies) and 10% FBS (referred to as complete RPMI 1640), and incubated for 4 h at 37° C. in a 5% $CO_2$ atmosphere before transfection with double-stranded siRNA molecules as described in Example 2, with a final concentration of siRNA of 600 nM. Each treatment was carried out in biological triplicate and the data presented is representative of a least two independent experiments. Several control samples were conducted as follows. The TLR9 agonist ODN2216 was obtained from InvivoGen (catalogue #tlrl-hodna) and added directly to the cells to a final concentration of 3 μM to control for pDCs activation and IFNα, production. The TLR8 agonist CL75 was added directly to the cells to a final concentration of 1 μg/ml. DOTAP alone (ie in the absence of any siRNA) was added to cells as a mock transfection control, to control for the non-specific effect of the transfection reagent. One control, the medium control, contained only cells in the complete RPMI medium described above, in the absence of other reagents.

TNFα Detection

Human TNFα in transfected cell supernatants was measured as described in Example 3.

IFNα Detection

Figure 4:
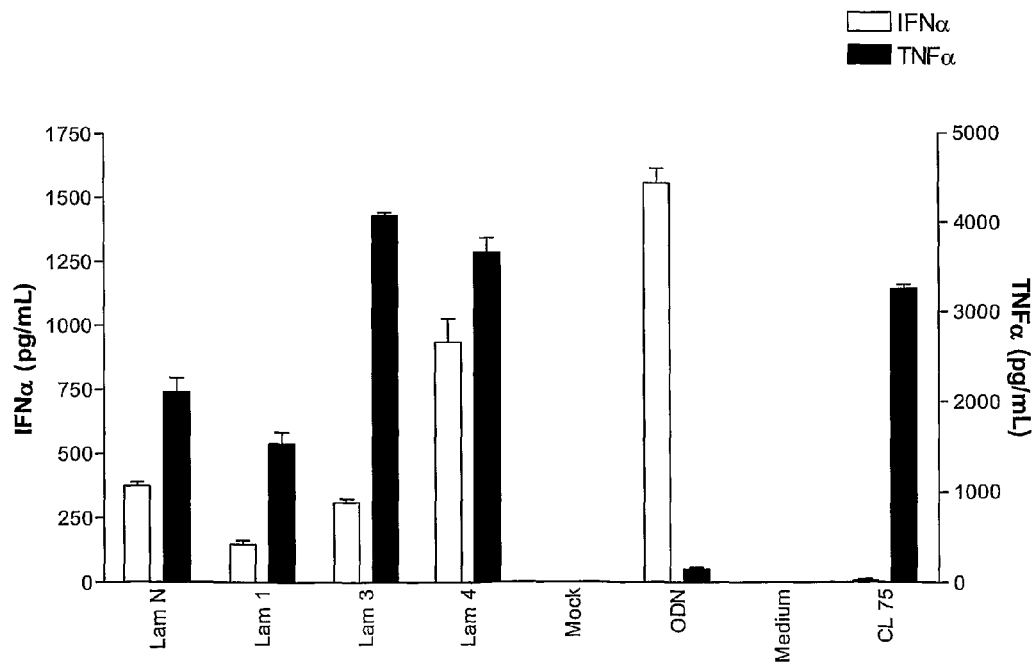
FIG. 4 provides a graph showing TNFα and IFNα expression in peripheral blood monocytic cells (PBMCs) following transfection with Lamin-targeting siRNA molecules.

Human IFNα in culture supernatants was quantified by sandwich ELISA using an mouse anti-human IFNα monoclonal antibody (0.5 μg/ml, 21112-1; PBL Biomedical, Piscataway, N.J., United States of America) and rabbit anti-human IFNα polyclonal antibody (0.5 μg/ml, 31130-1; PBL Biomedical). A goat anti-rabbit HRP-conjugated antibody (0.8 μg/ml, 31460; Pierce Thermo Fisher Scientific Inc, Rockford, Ill., United States of America) was used for detection. TMB substrate (T0440; Sigma-Aldrich) was used for quantification of INF-α on a Fluostar OPTIMA (BMG Labtech) plate reader. Results are shown in FIG. 4 with error bars representing the SEM.

Results and Discussion

IFNα is believed to be predominately induced by human TLR7 signalling and TNFα is believed to be mostly induced by human TLR8 signalling in human PBMCs (Gorden et al., 2005).

Experiments conducted using RAW (Example 2) and the THP-1 (Example 3) cell models indicates that both TLR7 and TLR8 signalling is induced by some of the siRNA molecules examined. TNFα expression in the RAW cell model is considered to be predictive of the levels of IFNα expected to be induced in PBMCs and TNFα expression in the THP-1 cell model is considered to be predictive for the level of TNFα expected to be induced in PBMCs, upon stimulation with the same siRNA molecules. However, the RAW cell and THP-1 cell models do not take into account the positive feedback mechanisms related to the presence of different cell subtypes in the blood. For instance, while macrophages produce TNFα, they also activate NK cells to become responsive to TLR8 agonists, resulting in the production of IFNγ (Hart et al., 2005). The present applicant has also recently reported activation of blood monocytes by IFNγ, rendering these cells more responsive to RNA molecules (Gantier et al., 2008), which results in higher levels of TNFα induction. For this reason it is advantageous and more sensitive to measure the immunostimulatory potential of siRNA molecules in human PBMCs, which fully reconstitutes the potential feedback mechanisms related to siRNA sensing by immune cells.

As shown in FIG. 4, in response to stimulation with LAM-1, PBMCs produced less IFNα and less TNFα than when stimulated with LAM-N, indicating that the LAM-1 modification is not beneficial to the overall level of immunostimulation. In comparison, LAM-3 induced slightly lower levels of IFNα and higher levels of TNFα than LAM-N, suggesting that the LAM-3 motif may be beneficial to the TNFα response induced by siRNA. Meanwhile, LAM-4 induced a marked increase in levels of both TNFα and IFNα when compared to LAM-N. This indicates that LAM-4 has higher immunostimulatory properties than LAM-N and supports the data from RAW and THP-1 cells that this response is associated with both TLR7 and TLR8 recruitment.

Example 5

Knockdown of Gene Expression by siRNA Molecules in HEK 293 T Cells

Materials and Methods siRNA

The double-stranded siRNA molecules used in this example were as described in Example 1, annealed as described in Example 2.

Cell Culture

HEK 293 T cells, a human embryonic kidney cell line, were cultured in DMEM complemented with 10% FCS and 1× antibiotic/antimycotic. RNAi experiments were performed in 24-well plates using a reverse transfection protocol as described below.

RNA Interference-Reverse Transfection Protocol

To prepare each treatment in triplicate, we complexed 4.5 μL of lipofectamine 2000 (11668; Invitrogen Life Technologies) in 300 μL of Opti-MEM (51985-034; Invitrogen Life Technologies) and added the siRNA molecules such that the final concentration of siRNA in each well was 10 nM. For the OptiMEM only treatment, no lipofectamine or siRNA was added. For the siControl condition, non-targeting siRNA control (#4635, Ambion) was used. After 20 min of incubation, 100 μl of the appropriate Lipofectamine 2000/siRNA/Opti-MEM mixture was added directly into each well. 100,000 HEK 293 T cells suspended in 500 μL of complete DMEM (including 10% FCS and 1× antibiotic/antimycotic) was added to each well giving a final volume of 600 μL per well. The plate was incubated for 24 hours at 37° C. in a 5% $CO_2$ atmosphere. The supernatants were discarded and the mRNA was immediately isolated from cells as detailed below.

Real-Time (RT) PCR mRNA was column-purified from cells using NucleoSpin RNAII columns (740955; Macherey-Nagel) according to the manufacturer's instructions. cDNA was synthesised from column-purified RNA using the SuperScript III First-Strand kit (18080-051; Invitrogen Life Technologies), with oligo-dT (20) priming and following the manufacturer's instructions. Real-time PCR was conducted with the iQ SYBR Green Supermix (170-8882; Bio-Rad) on a Bio-Rad iCycler. The DNA primers used were synthesised by Sigma-Proligo as described in Table 2. The reference gene was hGAPDH (NM_002046), and the primers used to amplify this gene are shown in Table 2.

TABLE 2

| Gene | Primer | 5'-3' sequence | SEQ ID |
|---|---|---|---|
| Lamin | LaminA-C-FWD | AGCAAAGTGCGTGAGGAGTT | SEQ ID NO. 8 |
| Lamin | LaminA-C-REV | GAGTTCAGCAGAGCCTCCAG | SEQ ID NO. 9 |
| GAPDH | GAPDH-FWD | CATCTTCCAGGAGCGAGATCCC | SEQ ID NO. 10 |
| GAPDH | GAPDH-REV | TTCACACCCATGACGAACAT | SEQ ID NO. 11 |

Each amplicon was sequence-verified and used to generate a standard curve for the quantification of gene expression.

Results and Discussion

Figure 5:
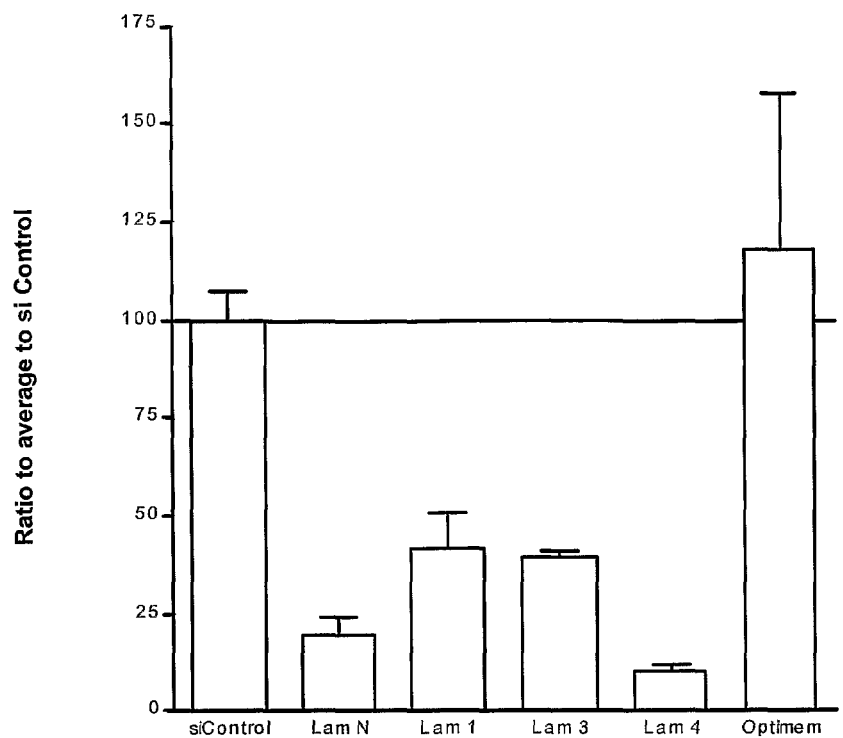
FIG. 5 provides a graph showing the relative level of gene silencing of the Lamin gene at the mRNA level in HEK 293 cells following RNAi with Lamin-targeting siRNA molecules.

As shown in FIG. 5, Lamin gene expression is markedly reduced by LAM-N, and even further reduced by LAM-4. In contrast, LAM-1 and LAM-3 showed lesser ability to silence Lamin gene expression, indicating that the modifications in LAM-1 and LAM-3 notably alter RNAi pathway recruitment.

Accordingly, LAM-4 is a suitable double-stranded siRNA molecule to both knock down gene expression and induce immunostimulation, and, in fact, the uridine bulge present on the sense strand seems to induce increased gene silencing capability compared to LAM-N, the double-stranded siRNA molecule with the native Lamin gene sequence. To investigate this possibility further, dose response gene silencing was conducted as described in Example 6 below.

Example 6

Optimising Knockdown of Gene Expression by siRNA Molecules in HEK 293 T Cells

Materials and Methods siRNA

The double-stranded siRNA molecules LAM-N and LAM-1 were used as described in Example 1.

Cell Culture

HEK 293 T cells were cultured as described in Example 5.

RNA Interference

RNA interference was performed as described in Example 5, except that the final concentration of the double-stranded siRNA molecules was varied to be 10 nM, 2 nM and 0.4 nM.

Results and Discussion

Figure 6:
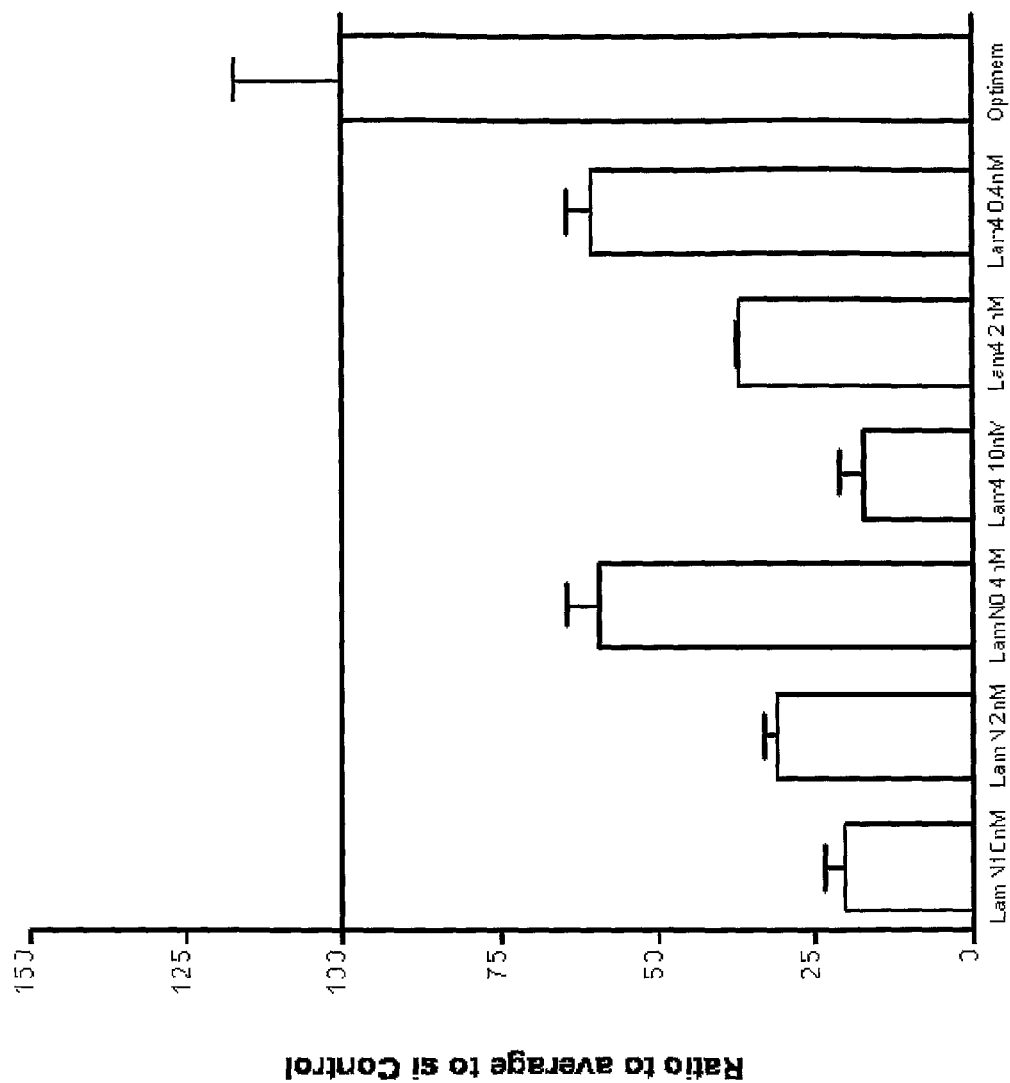
FIG. 6 provides a graph showing dose-response of gene silencing of the Lamin gene at the mRNA level in HEK 293 cells following transfection with Lamin-targeting siRNA molecules.

As shown in FIG. 6, LAM-N and LAM-4 inhibited Lamin gene expression in a similar dose-responsive manner. These results showed that 10 nM was the optimum concentration of siRNA for gene silencing of the conditions tested.

It is clear that LAM-4, with a uridine bulge on the sense strand of a double-stranded siRNA molecule, offers immunostimulation and is also capable of maintaining a similar level of gene silencing as the native sequence (LAM-N). Further, it is likely that the addition of uridine bulge to the sense strand may enhance or confer immunostimulatory activity to, potentially any double-stranded siRNA sequence, without substantially affecting the gene silencing ability of the antisense strand.

Example 7

Validation of the Effect of a Uridine Bulge in siRNA Molecules Targeting Enhanced Green Fluorescent Protein (EGFP)

Materials and Methods siRNA siRNA molecules targeting enhanced green fluorescent protein (EGFP) were designed so that the antisense strand contained the native sequence complementary to the EGFP mRNA, and the sense strand contained either the native sequence of the EGFP snRNA (ie EGFP-N siRNA), or were based on the native sequence of the EGFP mRNA except for the inclusion of a uridine bulge-containing sequence (ie EGFP-U siRNA). Further, the EGFP was designed to have a "Dicer substrate" structure (ie 25+0/+2 nucleotides in length, such that there is a two nucleotide overhang on the 3' end of the antisense (guide) strand, as shown schematically in FIG. 7A and FIG. 9. The EGFP-N siRNA molecule was designed using BioPredSi (Huesken et al., 2005). It was selected according to BioPredSi score (0.843655) and was predicted to be a poor agonist of TLR7/8 because of the low amount of uridylate nucleotides on both strands. The RNA molecules were synthesised as single-stranded molecules by Integrated DNA Technology (IDT; Coralville, Iowa, United States of America), and then annealed to form double-stranded siRNA molecules as described in Example 2 to a concentration of 40 μM. The sense (S) and antisense (AS) nucleotide sequences of the siRNA molecules are shown in Table 3.

TABLE 3

EGFP siRNA molecules

| siRNA duplex | siRNA single stranded molecule | 5'-3' Sequence | SEQ ID |
|---|---|---|---|
| EGFP-N | EGFP-N-S | GCGCCGAGGUGAAGUUCGAGGGCGA | SEQ ID NO. 12 |
| EGFP-N | EGFP-AS | UCGCCCUCGAACUUCACCUCGGCGCGG | SEQ ID NO. 13 |
| EGFP-U | EGFP-U-S | GCGCCGAGUUUUAGUUCGAGGGCGA | SEQ ID NO. 14 |
| EGFP-U | EGFP-AS | UCGCCCUCGAACUUCACCUCGGCGCGG | SEQ ID NO. 13 |

Bold font denotes polyuridine motif; <u>underlined</u> font denotes non-complementary sequence 293-GFP Cell Culture HEK293T cells stably expressing EGFP (293-GFP cells; gift from T. Sadler, Monash Institute of Medical Research, Clayton, Australia), were cultured in DMEM complemented with 10% FCS and 1× antibiotic/antimycotic (15240-062; Invitrogen Life Technologies). RNAi experiments were performed in 96-well black plates with clear bottom (BD Falcon #353948) using a reverse transfection protocol as described below.

RNAi Reverse Transfection Protocol

Lipofectamine 2000 (1.35 μL; 11668; Invitrogen Life Technologies) was complexed in 150 μL of Opti-MEM (51985-034; Invitrogen Life Technologies), and 1.5 μL of siRNA molecules (diluted to 4 μM in duplex buffer) was added such that the final concentration of siRNA in each well was 10 nM. For the "Medium" control, OptiMEM only was added to the wells (ie no lipofectamine or siRNA was added). For the "siControl" condition, non-targeting siRNA control (#4635, Ambion) was used. For "siGFP19+2" control condition, a published symmetric siRNA molecule previously shown to down-regulate EGFP expression (Marques et al., 2006) was used. After 20 min of incubation, 50 μl of the appropriate Lipofectamine 2000/siRNA/OptiMEM mixture was added directly into each well of the 96 well plate. 15,000 293-GFP cells suspended in 150 μL of complete DMEM (including 10% FCS and 1× antibiotic/antimycotic) was added to each well giving a final volume of 200 μL per well. The plate was cultured for 48 hours at 37° C. in a 5% CO$_2$ atmosphere and EGFP expression was measured as described below. Each treatment was performed in triplicate.

Fluorescent-Based Measure of EGFP Knock-Down

EGFP expression (and down-regulation) in 293-GFP cells following transfection with the EGFP siRNA molecules was measured using a Fluostar OPTIMA (BMG Labtech) plate reader. The supernatants were discarded and 50 µL of PBS was added to the cells. In order to correlate the amount of EGFP protein with fluorescent measurement from the plate reader, a two-fold dilution standard curve was generated by serially two-fold diluting a recombinant EGFP-fusion protein (gift from D. Wang, Monash Institute of Medical Research, Clayton, Australia) to cover a range from 150 ng/mL to 4.68 ng/mL in 50 µL PBS. The fluorescence from each well was correlated to a protein concentration and reported to the mean concentration of the Medium control condition. The result shown is an aggregated total of three independent experiments in biological triplicate.

PBMC Isolation

Fresh blood from healthy human male donors was collected in heparin-treated tubes, and submitted to Ficoll-Paque plus (17-1440-02; GE Healthcare) gradient purification following the manufacturer's guidelines to isolate PBMCs.

Transfection of Double-Stranded siRNA Molecules

Isolated PBMCs were plated in a 96-well plate at $2 \times 10^5$ cells/well in complete RPMI 1640, and incubated for 4 h at 37° C. in a 5% $CO_2$ atmosphere. The EGFP siRNA molecules (ie EGFP-U or the EGFP-N siRNA molecules) were then transfected into cells with DOTAP (1811177; Roche) as follows. DOTAP (3.74 µg/µl per 80 µM siRNA) was first diluted in RPMI 1640 (75 µl) for 5 min before mixing with an equal volume of RPMI 1640 containing the siRNA. The resulting mix was incubated for 10-30 min and 50 µl was then added per well, resulting in a final volume of 200 µl per well with either 250 nM, 500 nM, or 750 nM final concentration of siRNA. The plates were cultured for 16 hours at 37° C. in a 5% $CO_2$ atmosphere, and cell supernatants were then examined for concentration of TNFα and IFNα.

IFNα and TNFα Detection

The amount of human TNFα and IFNα present in transfected cell supernatants was examined as described in Example 3 and Example 4, respectively. Each treatment condition was carried out in biological triplicate; error bars represent the standard error of the mean (SEM). The results are shown as an aggregated total of four independent experiments on two different blood donors in biological triplicates.

Results and Discussion

Figure 7:
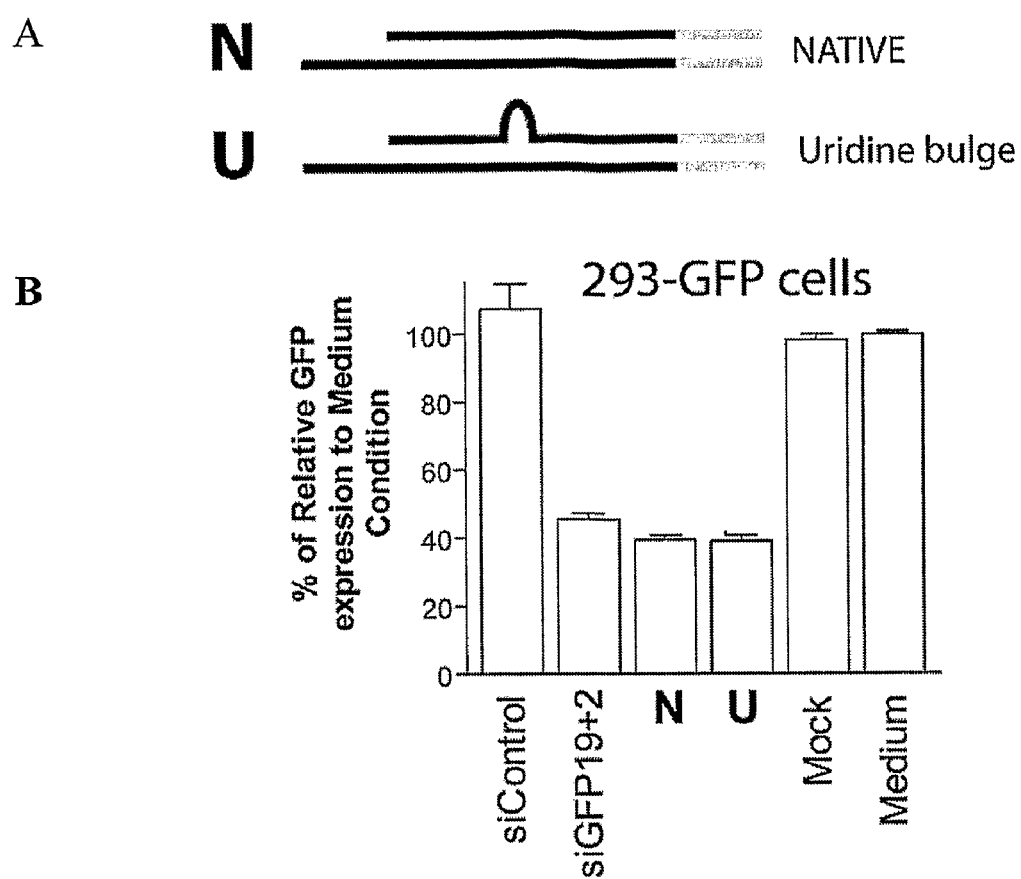
FIG. 7 provides (A) a schematic drawing of enhanced green fluorescent protein (EGFP)-targeting siRNA native (N) and uridine bulge-containing (U) molecules, and (B) a graph showing expression of EGFP in HEK 293T cells constitutively expressing EGFP following transfection with EGFP-targeting siRNA molecules.

As shown in FIG. 7B, both the EGFP-U and EGFP-N siRNA molecules knocked down expression of EGFP to a similar level as the control "SiGFP19+2" siRNA. This result confirms the ability of siRNA molecules with a uridine bulge to enter the RNAi pathway and silence gene expression. Accordingly, this experiment demonstrated the ability of siRNA molecules with a uridine bulge to down-regulate gene expression at the protein level by measurement of the fluorescent properties of EGFP.

FIG. 8A and FIG. 8B demonstrate the level of TNFα and IFNα, respectively, induced by increasing concentrations of the EGFP-N and EGFP-U siRNA molecules in human PBMC, showing the immunostimulatory ability of the molecules. Notably, the EGFP-N siRNA molecule possesses low immunostimulatory ability, while the EGFP-U siRNA molecule induced higher cytokines levels. Further, it was found that TNFα was induced at a higher level than IFNα, indicating that the immune stimulation is likely to be predominantely due to enhanced TLR8 recruitment by the uridine bulge-containing siRNA molecule.

Example 8

A Uridine Bulge in siRNA Molecules Increases Immunostimulation in Human PBMC

This example investigated whether four different uridine bulge-containing siRNA molecules affected immunostimulation (ie as compared to corresponding native siRNA molecules), as measured by the levels of 17 cytokines in PBMC cell supernatants following transfection with the siRNA molecules.

Materials and Methods siRNA

LAM-N and LAM-4 siRNA molecules were as described in Example 1; and EGFP-N and EGFP-U siRNA molecules were as described in Example 7. siRNA molecules targeting β-galactosidase (β-Gal) reporter gene (expressed by pSV-β-Galactosidase Control Vector, E1081; Promega Corporation, Madison, Wis., United States of America) and human papillomavirus (HPV) oncogene E7 were each designed so that the antisense strands contained the native complementary sequence of the gene being targeted, and the sense strand contained either the native sequence (ie β-Gal-N and E7-N, respectively) or was based on the native sequence except for the inclusion of a uridine bulge-containing sequence (ie β-Gal-U and E7-U, respectively). The E7 siRNA molecules were designed to have an asymmetric "Dicer substrate" structure (ie 25+0/+2 nucleotides in length, such that there is a two nucleotide overhang on the 3' end of the antisense (guide) strand). In contrast, the β-Gal siRNA molecules were designed to have a conventional symmetric 19+2 nucleotide structure, except that there is a two-nucleotide 'TT' DNA overhang on the 3' end of both the sense and antisense strands (indicated by "dTdT" in Table 4). The native β-Gal siRNA molecule had previously been shown to have low immunostimulatory properties (Judge et al., 2005). The RNA molecules were synthesised as single-stranded molecules by Integrated DNA Technology, and then annealed to form double-stranded siRNA molecules as described in Example 2 to a concentration of 40 µM. The sense (S) and antisense (AS) nucleotide sequences of the β-galactosidase and E7 siRNA molecules are shown in Table 4, and the siRNA molecules are schematically represented in FIG. 9.

TABLE 4

B-GAL and E7 siRNA molecules

| siRNA duplex | siRNA single-stranded molecule | 5'-3' Sequence | SEQ ID |
|---|---|---|---|
| B-GAL-N | B-GAL-N-S | UUAUGCCGAUCGCGUCAC AdTdT | SEQ ID NO. 15 |
| B-GAL-N | B-GAL-AS | UGUGACGCGAUCGGCAUA AdTdT | SEQ ID NO. 16 |
| B-GAL-U | B-GAL-U-S | UUAUGCCGUUUUCGUCAC AdTdT | SEQ ID NO. 17 |
| B-GAL-U | B-GAL-AS | UGUGACGCGAUCGGCAUA AdTdT | SEQ ID NO. 16 |

TABLE 4-continued

B-GAL and E7 siRNA molecules

| siRNA duplex | siRNA single-stranded molecule | 5'-3' Sequence | SEQ ID |
|---|---|---|---|
| E7-N | E7-N-S | ACCGGACAGAGCCCAUUACAAUAUU | SEQ ID NO. 18 |
| E7-N | E7-AS | AAUAUUGUAAUGGGCUCUGUCCGGUUC | SEQ ID NO. 19 |
| E7-U | E7-U-S | ACCGGACAUUUUCCAUUACAAUAUU | SEQ ID NO. 20 |
| E7-U | E7-AS | AAUAUUGUAAUGGGCUCUGUCCGGUUC | SEQ ID NO. 19 |

Bold font denotes polyuridine motif, <u>underlined</u> font denotes non-complementary sequence.

Cells and siRNA Transfection

PBMCs from two healthy male donors were isolated and transfected with the siRNA molecules directed against Lamin, EGFP, β-galactosidase and E7 (with or without a uridine bulge-containing sequence) as described in Example 7, except that siRNA molecules were transfected at 750 nM per well only. Experimental controls included "mock" transfections (ie transfection agent in the absence of siRNA) and TLR9 agonist (ODN) and TLR8 agonist (CL 75) controls were performed as described in Example 4 and 2, respectively.

Detecting Induced Cytokine Levels

A 50 μL aliquot of each post-treatment cell supernatant was assayed for cytokine levels using a 17 cytokine bead array (Bioplex solution array system, Bio-Rad Laboratories, Hercules, Calif., United States of America) according to the manufacturer's instructions. The data is from biological duplicates from two blood donors, the results of which were pooled for statistical analysis. The system utilises a suspension sandwich ELISA-like protocol, in which capture antibodies are coupled to spectrally distinct polystyrene beads (5 μm diameter). Each bead detects a different cytokine, using a biotinylated antibody, with streptavidin-phycoerytherin fluorophore used as a reporter complex. The Bio-Plex solution array system utilises a flow cytometry based technology to identify the bead (to determine which cytokine it is detecting) and a second signal obtained from the reporter complex to quantify cytokine levels. Cytokines measured were interleukin (IL)-1β, IL-2, IL-4, IL-5, IL-6, IL-7, IL-8, IL-10, IL-12 (p70), IL-13, IL-17, granulocyte-colony stimulating factor (G-CSF), granulocyte macrophage-colony stimulating factor (GM-CSF), IFNγ, monocyte chemoattractant protein (MCP)-1, macrophage inflammatory protein (MIP)-1β and TNFα. A standard curve was generated for each cytokine using a five-parameter logistic regression curve fit and cytokine concentrations were determined automatically using Bio-Plex Manager software (v4.01).

Statistical Analysis

There were four values (ie two wells per donor) for each experimental condition. For each cytokine, an ANOVA was first performed to determine whether there were significant differences between any of the groups. Where no significant difference was found, no further anaylsis was performed. Where statistical significance was found, individual t-tests were performed that compared for each siRNA set (ie the effect of the (N) native siRNA molecule against the corresponding (U) uridine bluge-containing siRNA molecule). The TLR9 (for positive control of activation of pDCs) and TLR8 agonists were compared to the mock transfection control.

Results and Discussion

The statistical analysis of the results is presented in Table 5.

TABLE 5

Statistical Analysis of cytokines induced by uridine bulge-containing siRNA molecules compared to corresponding native siRNA molecules

| Cytokine | ANOVA | LAM | EGFP | β-Gal | E7 | CL 75 | ODN | 3/4 significant immunostimulation* |
|---|---|---|---|---|---|---|---|---|
| IL-1β | 0.0001 | 0.002 | 0.001 | 0.001 | 0.022 | 0.0001 | 0.095 | Yes |
| IL-2 | 0.02 | 0.48 | 0.104 | 0.006 | 0.574 | 0.029 | 0.048 | No |
| IL-4 | 0.0001 | 0.003 | 0.002 | 0.013 | 0.022 | 0.004 | 0.008 | Yes |
| IL-5 | 0.001 | 0.108 | 0.034 | 0.005 | 0.025 | 0.009 | 0.765 | Yes |
| IL-6^ | 0.001 | 0.101 | 0.012 | 0.018 | 0.162 | 0.092 | 0.074 | No |
| IL-7 | 0.0001 | 0.011 | 0.057 | 0.004 | 0.028 | 0.0001 | 0.031 | Yes |
| IL-8# | 0.054 | — | — | — | — | — | — | — |
| IL-10 | 0.0001 | 0.016 | 0.013 | 0.199 | 0.064 | 0.0001 | 0.038 | No |
| IL12p70 | 0.0001 | 0.01 | 0.0001 | 0.0001 | 0.01 | 0.012 | 0.435 | Yes |
| IL13 | 0.710 | — | — | — | — | — | — | No |
| IL17 | 0.0001 | 0.016 | 0.029 | 0.01 | 0.054 | 0.019 | 0.065 | Yes |
| G-CSF | 0.0001 | 0.005 | 0.0001 | 0.05 | 0.602 | 0.0001 | 0.001 | Yes |
| GM-CSF | 0.0001 | 0.01 | 0.001 | 0.008 | 0.024 | 0.0001 | 0.002 | Yes |
| IFNγ | 0.0001 | 0.004 | 0.001 | 0.015 | 0.016 | 0.0001 | 0.002 | Yes |
| MCP-1# | 0.002 | 0.391 | 0.352 | 0.391 | 0.420 | 0.223 | 0.705 | — |
| MIP-1β# | 0.0001 | — | 0.182 | — | — | 0.182 | 0.207 | — |
| TNFα | 0.0001 | 0.008 | 0.000 | 0.023 | 0.023 | 0.015 | 0.002 | Yes |

Figure 10:
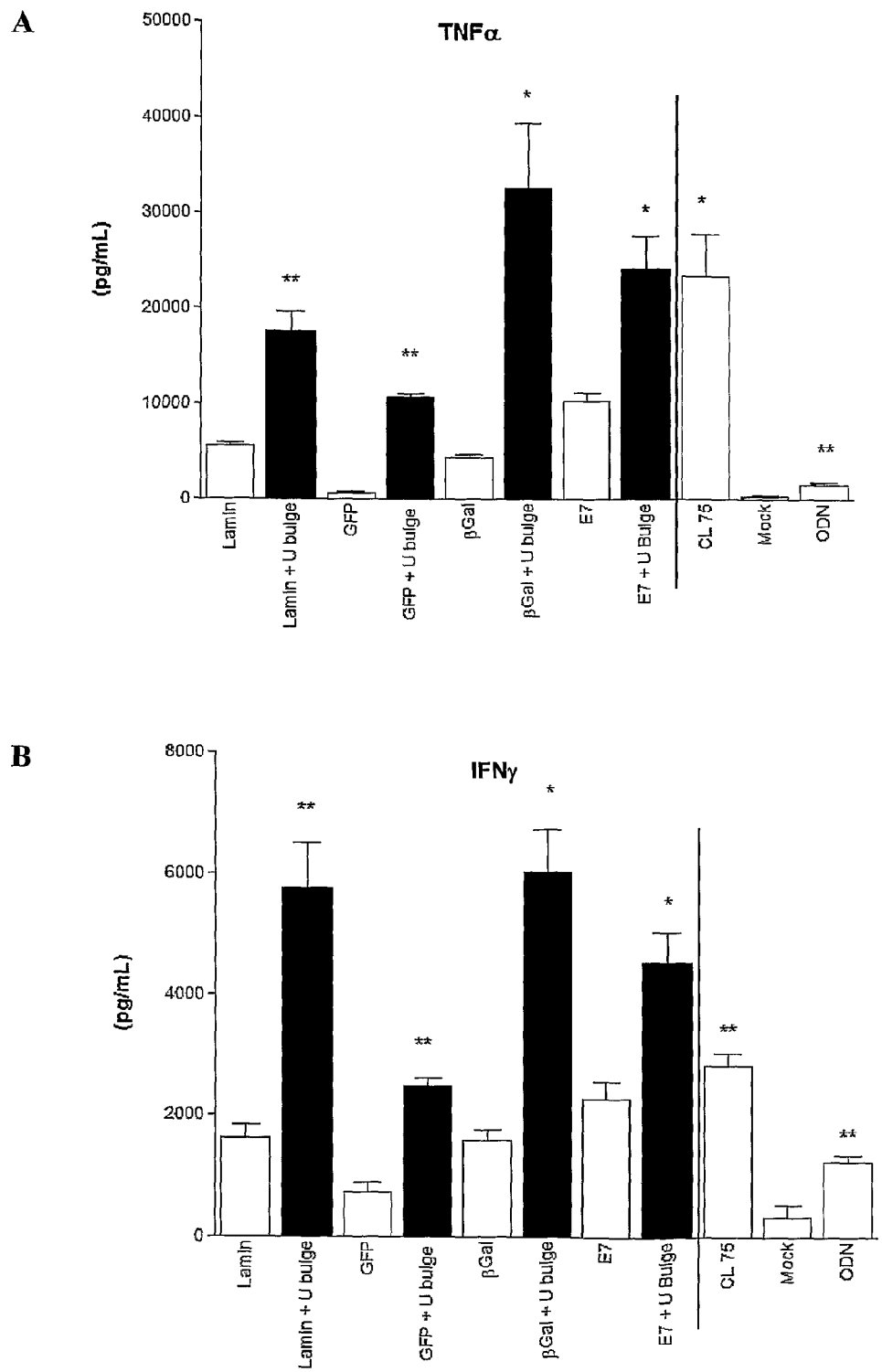
FIG. 10 provides graphs of (A) TNFα, (B) IFNγ, (C) IL-1β, (D) IL-7, (E) IL-12(p70), (F) IL-17, (G) IL-4, (H) IL-5, (I) G-CSF, and (J) GM-CSF levels in PBMC supernatants following transfection with native (N) and uridine bulge-containing (U) siRNA molecules targeted to Lamin, EGFP, B-galactosidase, and E7 genes, where * represents $p<0.05$ when the N siRNA is compared to the corresponding U siRNA and where ** represents $p<0.01$ when the N siRNA is compared to the corresponding U siRNA.
Figure 10:
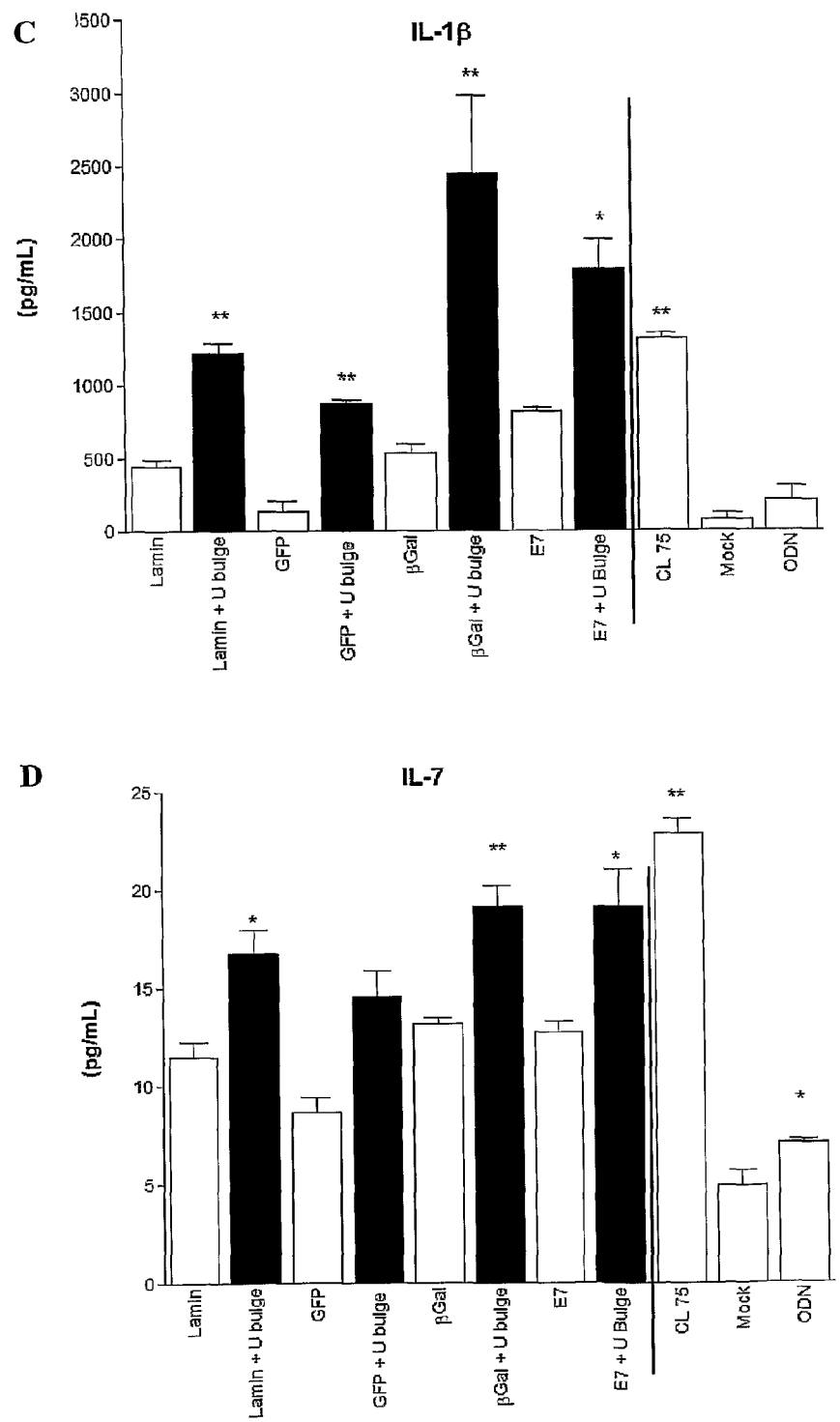
Figure 10:
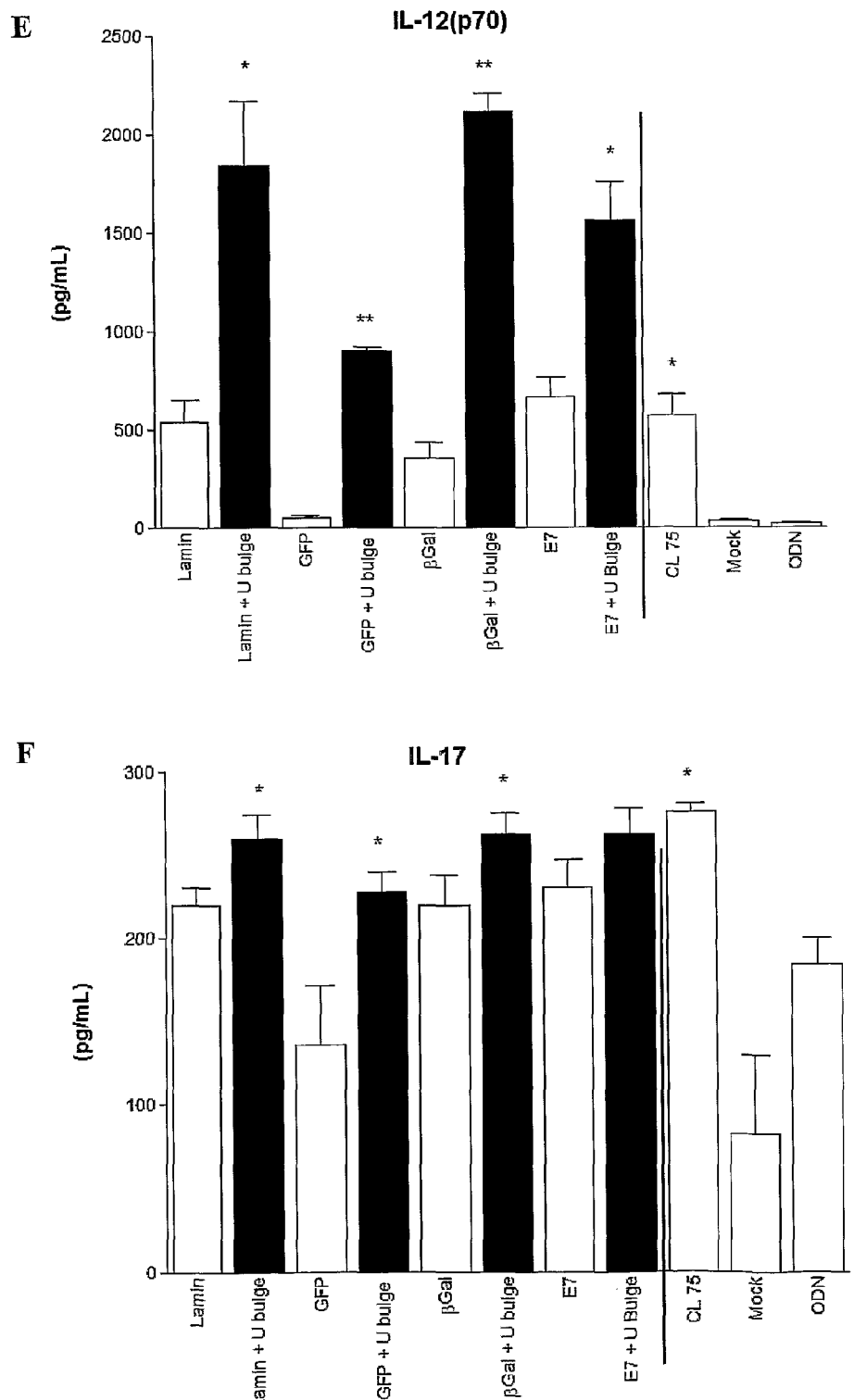
Figure 10:
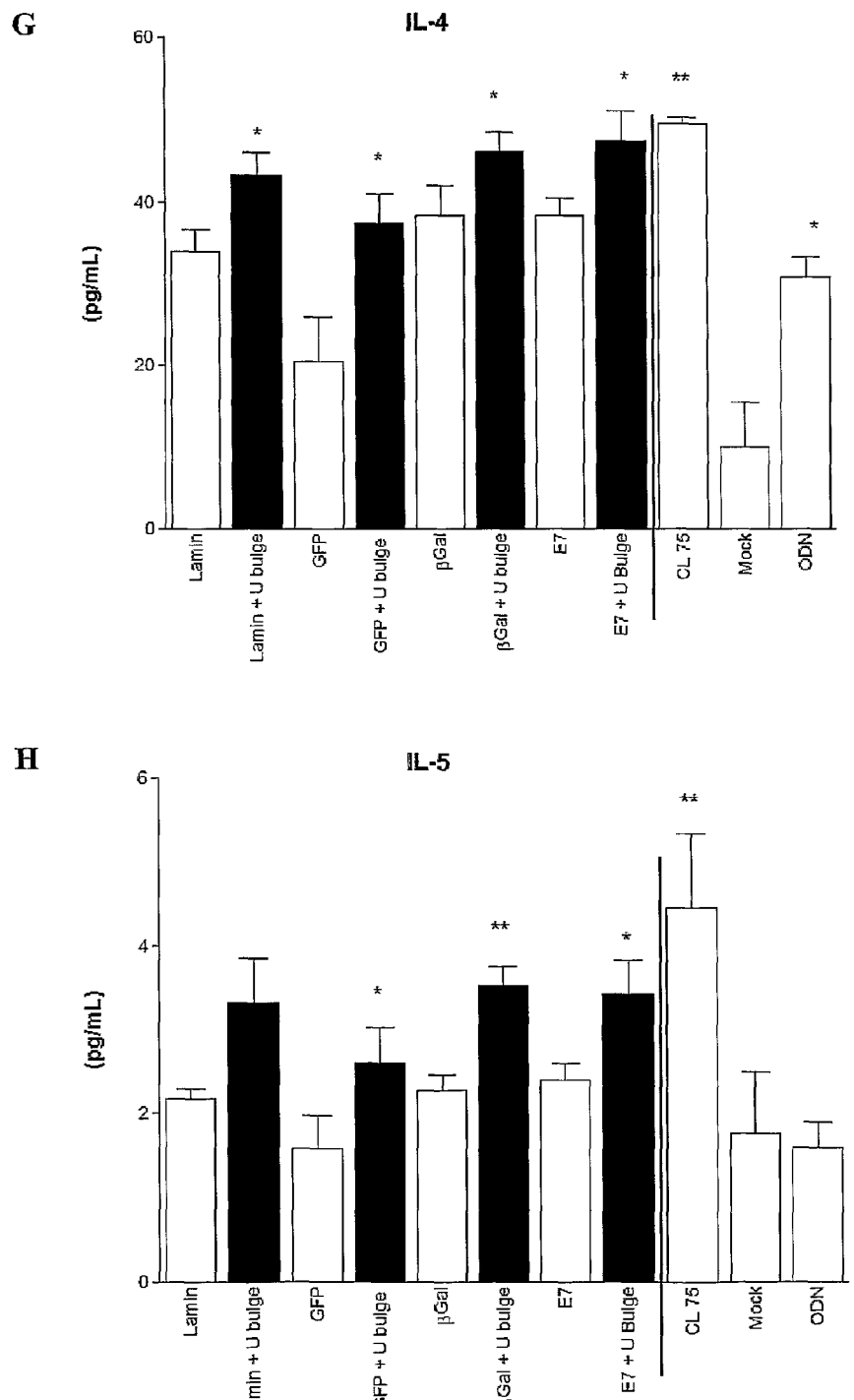
Figure 10:
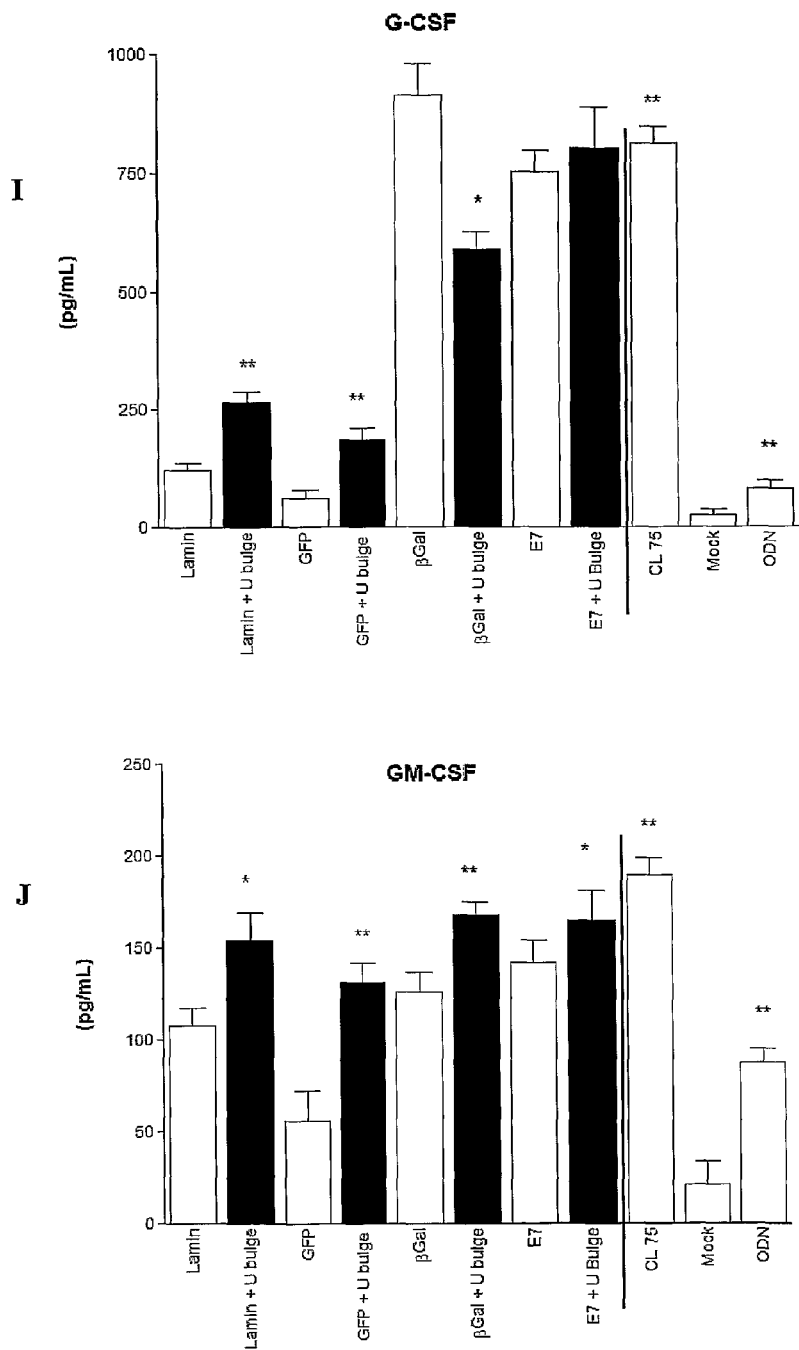

*3/4 significant immunostimulation = ≧3 of 4 siRNA sets tested showed a significant increase in immunostimulation induced by the "U" siRNA compared to the "N" siRNA;

Most of the values obtained for these cytokines were above that of the standard curve and their concentrations could not be accurately extrapolated;

^Some of the values obtained for IL-6 were above standard curve linear range (eg for LAM, E7 and CL75), effecting the significance of the increase in IL-6 levels induced by the "U" siRNA compared to the "N" siRNA.

Where at least three of the four tested sets of siRNA molecules showed an induction of a significant increase in cytokine levels for the "U" siSRNA compared to the "N" siRNA, the induced cytokine levels are shown in FIG. 10. The cytokines that were significantly induced by the "U" siRNA compared to the "N" siRNA in at least three of the four siRNA sets were TNFα (FIG. 10A), IFNγ (FIG. 10B), IL-1β(FIG. 10C), IL-7 (FIG. 10D), IL-12(p70) (FIG. 10E), IL-17 (FIG. 10F), IL-4 (FIG. 10G), IL-5 (FIG. 10H), G-CSF (FIG. 10I), and GM-C SF (FIG. 10J).

Accordingly, the addition of the uridine bulge to the siRNA molecule increases expression of at least 10 of the 14 cytokines assayed by Bioplex for which accurate results were obtained. Additionally, IFNα was significantly up-regulated by the "U" siRNA compared to the "N" siRNA for all four tested sets of siRNA molecules using a specific IFNα ELISA as described in Example 3 (data not shown). It is of particular interest that cytokines such as TNFα, IFNα and IFNγ are significantly up-regulated by the presence of the uridine bulge, as these cytokines are reputed to have anti-tumour effects.

The β-GAL-N siRNA molecule was previously published to have low immunostimulatory potential (β-Gal-924; Judge et al. 2005). The symmetric 19+2-nucleotide β-Gal siRNA design, with its "TT" 3' overhang, is notably not a "Dicer substrate". However, this 19+2 siRNA design is frequently used currently as it is thought to mimic the natural product obtained following Dicer processing of long dsRNAs (Elbashir et al., 2001). The results indicate that the addition of a uridine bulge to the β-Gal siRNA molecule induced immunostimulation, indicating that the addition of the uridine bulge may enhance immunostimulation of, potentially, any siRNA molecule, regardless of its design. Of interest, this effect is, accordingly, not limited to "Dicer substrates" but can also be applied to shorter siRNA molecules.

Example 9

Uridine Bulge in siRNA Molecules Induces Stronger TNFα Response in Human Monocytes Compared to Mouse Macrophages Materials and Methods
siRNA
EGFP-N and EGFP-U siRNA molecules were as described in Example 7.
Cells and siRNA Transfection
Human CD14+ monocytes were isolated as follows. Blood was obtained from two healthy male donors and the buffy coat submitted to a Ficoll-Paque plus (17-1440-02; GE Healthcare) gradient purification following the manufacturer's instructions. Monocytes were separated using counter-flow centrifugation elutriation (which separates cells on sedimentation properties, ie size/density, in a centrifuge with aspiration device) and the CD14+ population was further isolated by fluorescence-activated cell sorting (FACS) using standard methods. Isolated cells were then plated in a 96-well plate at 25,000 cells/well in complete RPMI 1640, and incubated for 1 h at 37° C. in a 5% $CO_2$ atmosphere before transfection with 500 nM siRNA complexed with DOTAP as described in Example 7 and incubated overnight at 37° C. in a 5% $CO_2$ atmosphere.

Figure 11:
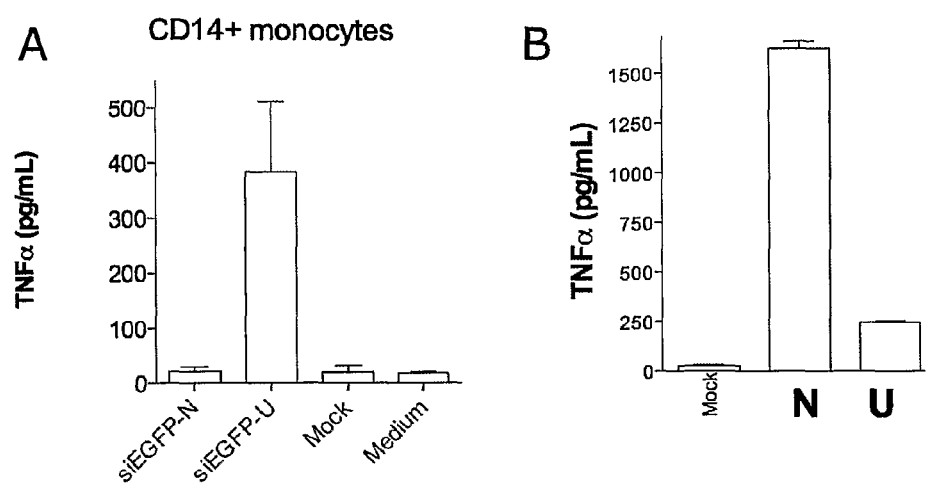
FIG. 11 provides graphs of TNFα levels in (A) human $CD14^+$ monocytes and (B) murine bone-derived macrophages following transfection with EGFP-targeting native (N) and uridine bulge-containing (U) siRNA molecules.

Bone marrow-derived murine macrophages were obtained as follows. Bone marrow was extracted from a wild type B6/C57 mouse and differentiation of the bone marrow cells carried out following standard methods. Briefly, femurs were flushed with complete RPMI 1640, and cells were plated in complete RPMI 1640 supplemented with $10^4$ U/ml recombinant human colony stimulating factor (rhCSF)-1 (a gift from DA Hume, Centre for Molecular Biology and University of Biotechnology, Brisbane, QLD, Australia) on 10 cm bacteriological plastic plates for 6 days at 37° C. in a 5% $CO_2$ atmosphere. On day 6, the cells were collected by scraping and plated in 96 well-plate (80,000 cells per well in 150 μl complete RPMI 1640 with $10^4$ U/ml rhCSF-1). The following day (day 7), the cells were transfected with 750 nM of siRNA complexed with DOTAP as described in Example 7 and incubated overnight at 37° C. in a 5% $CO_2$ atmosphere. All treatments were performed in biological triplicates, and error bars represent the standard error of the mean (SEM).
TNFα Detection
Mouse TNFα was detected in transfected cell supernatants as described in Example 2. Human TNFα was detected in transfected cell supernatants as described in Example 3.
Results and Discussion
As shown in FIG. 11A, EGFP-U siRNA markedly increased TNFα expression compared to the EGFP-N siRNA in human CD 14+ monocytes. By contrast, TNFα expression is lower in bone-derived murine macrophages induced by EGFP-U siRNA compared to the EGFP-N siRNA, as shown in FIG. 11B.

This data demonstrates that CD14+ monocytes are more susceptible to immunostimulation by the uridine bulge-containing siRNA molecules than are the murine macrophages. CD14+ monocytes are more responsive to TLR8 agonists than TLR7 agonists (Gorden et al., 2005), therefore, this data indicates that TLR8 is involved in the detection of the uridine bulge modification in human PBMCs. This finding is consistent with the preferential increase of TNFα over IFNα in human PBMCs stimulated with EGFP-U siRNA as shown in FIG. 8.

Additionally, in murine bone marrow-derived macrophages, the uridine bulge-containing siRNA molecule reduced the level of TNFα expression induced compared to the native siRNA molecule. It has been reported that siRNA sensing exclusively relies on TLR7 in these cells (Hornung et al., 2005). A similar trend, although not as pronounced, was seen with LAM-4 as well as with and another siRNA sequence containing a uridine bulge (results not shown). Whilst not wanting to be bound by theory, these results indicate that human TLR8 is preferentially recruited by the presence of a uridine bulge in siRNA molecules in human monocytes/macrophages.

Example 10

A Uridine Bulge in siRNA Molecules Enhances Immunostimulation in Poorly Immunostimulatory siRNA Molecules Materials and Methods
siRNA
EGFP-N and EGFP-U siRNA molecules were as described in Example 7. Human B-cell lymphoma (Bcl)-2 like (L)-12 (ie BCL2L12; GeneID: 75736) targeting siRNA molecules were designed so that the antisense strand contained the native complementary sequence of the BCL2L12 gene, and the sense strand contained either the native sequence (ie L-12-N siRNA) or was based on the native sequence except for the inclusion of a uridine bulge-containing sequence (ie L-12-U siRNA). The L-12 siRNA molecule was designed to have a "Dicer substrate" structure (ie 25+0/+2 nucleotides in length, such that there is a two-nucleotide overhang on the 3' end of the antisense (guide) strand). The RNA molecules were synthesised as single-stranded molecules by Integrated DNA Technology, and then annealed to form double-stranded siRNA molecules as described in Example 2. The sense (S) and antisense (AS) nucleotide sequences of the L-12 siRNA molecules are shown in Table 6. The 3' end of the L-12-N siRNA has a two-nucleotide 'CT' DNA overhang on the 3' end of the sense strand of the (indicated by "dCdT" in Table 6), which is believed to assist orientation of the siRNA within Dicer to enhance recognition of the sense strand as the passenger strand.

TABLE 6

IL-12 siRNA molecules

| siRNA duplex | siRNA single-stranded molecule | 5'-3' Sequence | SEQ ID |
|---|---|---|---|
| L12-N | L12-N-S | GCUGGUCCGCCUGUCCUC CGACUdCdT | SEQ ID NO. 21 |
| L12-N | L12-AS | AGAGUCGGAGGACAGGCG GACCAGCUU | SEQ ID NO. 22 |
| L12-U | L12-U-S | GCUGGUCCUUUUGUCCUC CGACUCU | SEQ ID NO. 23 |
| L12-U | L12-AS | AGAGUCGGAGGACAGGCG GACCAGCUU | SEQ ID NO. 22 |

Bold font denotes polyuridine motif, underlined font denotes non-complementary sequence.

Cells, Transfection and TNFα Detection

PBMCs were isolated from two healthy males donors as described in Example 7. PBMC were transfected with either 250 nM, 500 nM or 750 nM of siRNA molecules complexed with DOTAP using the method described in Example 7. TNFα was detected as described in Example 3. The results shown are from one blood donor in biological triplicates, but representative of two blood donors. Error bars represent the standard error of the mean (SEM). Mock, media and CL75 controls were set up as described above.

Results and Discussion

Figure 12:
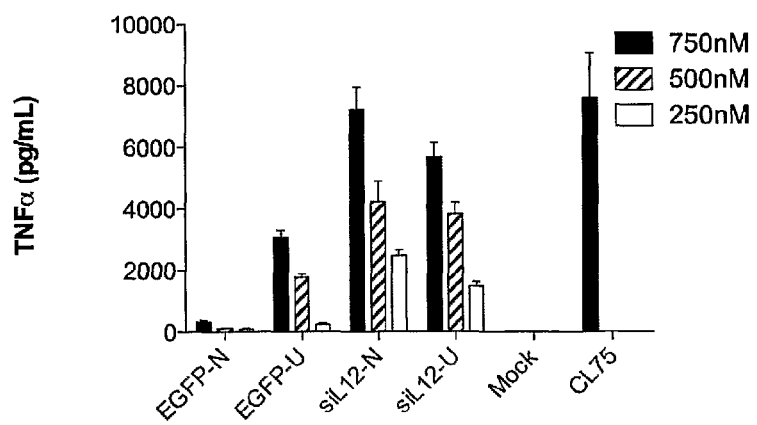
FIG. 12 provides a graph of TNFα levels in PBMCs following transfection with EGFP-targeting or B cell lymphoma (BCL)-2-like (L)-12 (ie BCL2L12)-targeting native (N) and uridine bulge-containing (U) siRNA molecules.

As shown in FIG. 12, EGFP-U siRNA increased the expression of TNFα compared to the EGFP-N siRNA at all concentrations of siRNA tested. In contrast, the L-12-U siRNA did not further increase the expression of TNFα above the L-12-N siRNA molecule at any concentrations of siRNA tested. However, the results indicate that the L-12-N siRNA molecule is highly immunostimulatory, as it induces a similar level of TNFα as the TLR8 agonist CL75; whereas the EGFP-N siRNA molecule appears to be poorly immunostimulatory, even at the highest concentrations of siRNA. Whilst not wanting to be bound by theory, this result indicates that the uridine bulge may not further enhance siRNA sequences that are highly immunostimulatory in their native form. However, it is also notable that the addition of the uridine bulge to the L-12 siRNA did not induce a significant reduction in immunostimulation, thereby indicating that the uridine bulge can potentially be added to any siRNA sequences without decreasing immunostimulation in human PBMCs, and therefore, TLR7/8 recruitment.

Although a preferred embodiment(s) of the present invention has been described in the foregoing detailed description, it will be understood that the invention is not limited to the embodiment(s) disclosed, but is capable of numerous rearrangements, modifications and substitutions without departing from the scope of the invention.

Throughout this specification the word "comprise", or variations such as "comprises" or "comprising" will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

REFERENCES

Allerson C R, Sioufi N, Jarres R, Prakash T P, Naik N, Berdeja A, Wanders L, Griffey R H, Swayze E E, Bhat B. (2005) Fully 2'-modified oligonucleotide duplexes with improved in vitro potency and stability compared to unmodified small interfering RNA. *J. Med. Chem.* 48: 901-904.

Choung S, Kim Y J, Kim S, Park H O, Choi Y C. (2006) Chemical modification of siRNAs to improve serum stability without loss of efficacy. *Biochem. Biophys. Res. Commun* 342: 919-927.

de Fougerolles A, Manoharan M, Meyers R, Vornlocher H P. (2005) RNA interference in vivo: toward synthetic small inhibitory RNA-based therapeutics. *Methods Enzymol.* 392: 278-296.

Diebold S S, Kaisho T, Hemmi H, Akira S, Reis e Sousa C. (2004) Innate antiviral responses by means of TLR7-mediated recognition of single-stranded RNA. *Science* 303: 1529-1531.

Diederichs S, Haber D A. (2007) Dual role for Argonautes in microRNA processing and posttranscriptional regulation of microRNA expression. *Cell* 131:1097-1108.

Elbashir S M, Harborth J, Lendeckel W, Yalcin A, Weber K, Tuschl T. (2001) Duplexes of 21-nucleotide RNAs mediate RNA interference in cultured mammalian cells. *Nature.* 411(6836):494-8.

Gantier M P, Tong S, Behlke M A, Xu D, Phipps S, Foster P S, Williams B R: (2008) TLR7 Is Involved in Sequence-Specific Sensing of Single-Stranded RNAs in Human Macrophages. *J. Immunol.* 180(4):2117-2124.

Gorden K B, Gorski K S, Gibson S J, Kedl R M, Kieper W C, Qiu X, Tomai M A, Alkan S S, Vasilakos J P. (2005) Synthetic TLR agonists reveal functional differences between human TLR7 and TLR8. *J. Immunol.* 174: 1259-1268.

Hannon G J, Rossi J J. (2004) Unlocking the potential of the human genome with RNA interference. *Nature* 431: 806-811.

Hart O M, Athie-Morales V, O'Connor G M, Gardiner C M. (2005) TLR7/8-mediated activation of human NK cells results in accessory cell-dependent IFNgamma production. *J Immunol.* 175(3):1636-1642.

Heil F, Hemmi H, Hochrein H, Ampenberger F, Kirschning C, Akira S, Lipford G, Wagner H, Bauer S. (2004) Species-specific recognition of single-stranded RNA via toll-like receptor 7 and 8. *Science* 303: 1526-1529.

Hemmi H, Kaisho T, Takeuchi O, Sato S, Sanjo H, Hoshino K, Horiuchi T, Tomizawa H, Takeda K, Akira S. (2002) Small anti-viral compounds activate immune cells via the TLR7 MyD88-dependent signaling pathway. *Nat. Immunol.* 3: 196-200.

Hornung V, Guenthner-Biller M, Bourquin C, Ablasser A, Schlee M, Uematsu S, Noronha A, Manoharan M, Akira S, de Fougerolles A, Endres S, Hartmann G. (2005) Sequence-specific potent induction of IFNalpha by short interfering RNA in plasmacytoid dendritic cells through TLR7. *Nat. Med.* 11: 263-270.

Huesken D, Lange J, Mickanin C, Weiler J, Asselbergs F, Warner J, Meloon B, Engel S, Rosenberg A, Cohen D, Labow M, Reinhardt M, Natt F, Hall J. (2005) Design of a genome-wide siRNA library using an artificial neural network. *Nat. Biotechnol.* 23(8):995-1001.

Hume, D A, Underhill D M, Sweet M J, Ozinsky A O, Liew F Y, Aderem A. (2001) Macrophages exposed continuously to lipopolysaccharide and other agonists that act via Toll-like receptors exhibit a sustained and additive activation state. *BMC Immunol.* 2:11.

Judge A D, Sood V, Shaw J R, Fang D, McClintock K, MacLachlan I. (2005) Sequence-dependent stimulation of the mammalian innate immune response by synthetic siRNA. *Nat. Biotechnol.* 23(4):457-62.

Jurk, M, Heil F, Vollmer J, Schetter C, Krieg A M, Wagner H, Lipford G, Bauer S. (2002) Human TLR 7 or TLR 8 independently confer responsiveness to the antiviral compound R-848. *Nat. Immunol.* 3: 499.

Jurk M, Kritzler A, Schulte B, Tluk S, Schetter C, Krieg A M, Vollmer J. (2006) Modulating responsiveness of human TLR 7 and 8 to small molecule ligands with T-rich phosphorothioate oligodeoxynucleotides. *Eur. J. Immunol.* 36: 1815-1826.

Karikó K, Bhuyan P, Capodici J, Weissman D (2004) Small interfering RNAs mediate sequence-independent gene suppression and induce immune activation by signaling through toll-like receptor 3. *J Immunol.* 172(11):6545-6549.

Khvorova A, Reynolds A, Jayasena S D (2003) Functional siRNAs and miRNAs exhibit strand bias. *Cell* 115(2):209-216. {Erratum in: *Cell* (2003) 115(4):505}.

Kim D H, Behlke M A, Rose S D, Chang M S, Choi S, Rossi J J. (2005) Synthetic dsRNA Dicer substrates enhance RNAi potency and efficacy. *Nat. Biotechnol.* 23(2):222-226.

Kubo T, Zhelev Z, Ohba H, Bakalova R. (2008) Chemically modified symmetric and asymmetric duplex RNAs: an enhanced stability to nuclease degradation and gene silencing effect. *Biochem. Biophys. Res. Commun.* 365(1):54-61.

Layzer J M, McCaffrey A P, Tanner A K, Huang Z, Kay M A, Sullenger B A. (2004) In vivo activity of nuclease-resistant siRNAs. *RNA* 10: 766-771.

MacDiarmid J A, Mugridge N B, Weiss I C, Phillips L, Burn A L, Paulin R P, Haasdyk J E, Dickson K A, Brahmbhatt V N, Pattison S T, James A C, Al Bakri G, Straw R C, Stillman B, Graham R M, Brahmbhatt H. (2007) Bacterially derived 400 nm particles for encapsulation and cancer cell targeting of chemotherapeutics. *Cancer Cell* 11(5):431-445.

Marques J T, Williams B R. (2005) Activation of the mammalian immune system by siRNAs. *Nat Biotech* 23(11): 1399-1405.

Marques J T, Devosse T, Wang D, Zamanian-Daryoush M, Serbinowski P, Hartmann R, Fujita T, Behlke M A, Williams B R. (2006) *Nat. Biotechnol.* A structural basis for discriminating between self and nonself double-stranded RNAs in mammalian cells. 24(5):559-565.

McIntyre and Fanning (2006) BMC Biotechnology Design and cloning strategies for constructing shRNA expression vectors. *BMC Biotechnology* 6:1

Rose S D, Kim D H, Amarzguioui M, Heidel J D, Collingwood M A, Davis M E, Rossi J J, Behlke M A. (2005) Functional polarity is introduced by Dicer processing of short substrate RNAs. *Nucleic Acids Res.* 33(13):4140-4156.

Sipa K, Sochacka E, Kazmierczak-Baranska J, Maszewska M, Janicka M, Nowak G, Nawrot B. (2007) Effect of base modifications on structure, thermodynamic stability, and gene silencing activity of short interfering RNA. *RNA* 13(8):1301-1316.

Sioud M. (2005) Induction of inflammatory cytokines and interferon responses by double-stranded and single-stranded siRNAs is sequence-dependent and requires endosomal localization. *J Mol Biol* 348:1079-1090.

Sioud M, Sorensen D R. (2003) Cationic liposome-mediated delivery of siRNAs in adult mice. *Biochem Biophys Res Commun.* 312(4):1220-1225.

Sledz C A, Holko M, de Veer M J, Silverman R H, Williams B R. (2003) Activation of the interferon system by short-interfering RNAs. *Nat. Cell Biol.* 5(9):834-839.

Varani G, McClain W H. (2000) The G×U wobble base pair. A fundamental building block of RNA structure crucial to RNA function in diverse biological systems. *EMBO Rep.* 1(1):18-23.

Yoneyama M, Kikuchi M, Natsukawa T, Shinobu N, Imaizumi T, Miyagishi M, Taira K, Akira S, Fujita T. (2004) The RNA helicase RIG-I has an essential function in double-stranded RNA-induced innate antiviral responses. *Nat Immunol.* 5(7):730-737.

The invention claimed is:

1. An isolated or synthesized double-stranded siRNA molecule comprising a sense strand and an antisense strand, wherein:
   the siRNA molecule comprises blunt and/or 3' overhanging ends at each end of the siRNA molecule;
   the antisense strand comprises a first nucleotide sequence that is at least 25 nucleotides in length, wherein said antisense strand is specifically complementary to mRNA transcribed from a target gene, and
   the sense strand comprises a second nucleotide sequence that is substantially or perfectly complementary to the antisense strand with the exception that the second nucleotide sequence comprises at least one centrally located immunostimulatory motif comprising two or more non-complementary nucleotides, wherein each non-complementary nucleotide is mismatched with a corresponding nucleotide of the antisense strand.

2. The siRNA molecule of claim 1, wherein said at least one immunostimulatory motif comprises three to five non-complementary nucleotides.

3. The siRNA molecule of claim 1, wherein said at least one immunostimulatory motif consists of nucleotides selected from guanylate and uridylate.

4. The siRNA molecule of claim 1, wherein said at least one immunostimulatory motif comprises a polyuridine motif.

5. The siRNA molecule of claim 4, wherein said polyuridine motif consists of a UUUU motif.

6. The siRNA of claim 1, further comprising one or more additional types of immunostimulatory motif including guanine- and uridine-rich sequence and/or GU motifs selected from the group consisting of GGUU, UUGGUG, UUGGUU, UGUGU and GUCCUUCAA motifs.

7. The siRNA molecule of claim 1, wherein the antisense strand has a two-nucleotide overhang at the 3' terminus of the antisense strand.

8. The siRNA molecule of claim 1, wherein the siRNA molecule is between 25+2 and 32+2 nucleotides in length.

9. The siRNA molecule of claim 1, wherein the siRNA molecule is between 25+0/+2 and 32+0/+2 nucleotides in length.

10. The siRNA molecule of claim 9, wherein the siRNA molecule is 25+0/+2 nucleotides in length.

11. An expression cassette or vector for transcription of an intermediate RNA molecule capable of being processed by a cell into a double-stranded siRNA molecule of claim 1.

12. A composition for introducing an siRNA molecule into a cell, said composition comprising the siRNA molecule of claim 1, optionally in combination with a pharmaceutically- or veterinary-acceptable carrier.

13. The siRNA molecule of claim 1, wherein the immunostimulatory motif is located at a site comprising nucleotide positions 9 to 12 from the 5' terminus of the sense strand.

14. The siRNA molecule of claim 10, wherein the immunostimulatory motif is located at a site comprising nucleotide positions 9 to 12 from the 5' terminus of the sense strand.

\* \* \* \* \*

SEQUENCE LISTING

<160> NUMBER OF SEQ ID NOS: 23

<210> SEQ ID NO 1
<211> LENGTH: 25
<212> TYPE: RNA
<213> ORGANISM: Artificial Sequence
<220> FEATURE:
<223> OTHER INFORMATION: LAM-N

<400> SEQUENCE: 1
gaaggagggu gaccugauag cugcu                                            25

<210> SEQ ID NO 2

```
<211> LENGTH: 27
<212> TYPE: RNA
<213> ORGANISM: Artificial Sequence
<220> FEATURE:
<223> OTHER INFORMATION: LAM-NAS

<400> SEQUENCE: 2
agcagcuauc aggucacccu ccuucuu                                              27

<210> SEQ ID NO 3
<211> LENGTH: 25
<212> TYPE: RNA
<213> ORGANISM: Artificial Sequence
<220> FEATURE:
<223> OTHER INFORMATION: LAM-1S

<400> SEQUENCE: 3
gaaggagggu gaccugauaa accaa                                                25

<210> SEQ ID NO 4
<211> LENGTH: 27
<212> TYPE: RNA
<213> ORGANISM: Artificial Sequence
<220> FEATURE:
<223> OTHER INFORMATION: LAM-1AS

<400> SEQUENCE: 4
uugguuuauc aggucacccu ccuucuu                                              27

<210> SEQ ID NO 5
<211> LENGTH: 25
<212> TYPE: RNA
<213> ORGANISM: Artificial Sequence
<220> FEATURE:
<223> OTHER INFORMATION: LAM-3S

<400> SEQUENCE: 5
gaaggagggu gaccugauag guuac                                                25

<210> SEQ ID NO 6
<211> LENGTH: 27
<212> TYPE: RNA
<213> ORGANISM: Artificial Sequence
<220> FEATURE:
<223> OTHER INFORMATION: LAM-3AS

<400> SEQUENCE: 6
gugguuuauc aggucacccu ccuucuu                                              27

<210> SEQ ID NO 7
<211> LENGTH: 25
<212> TYPE: RNA
<213> ORGANISM: Artificial Sequence
<220> FEATURE:
<223> OTHER INFORMATION: LAM-4S

<400> SEQUENCE: 7
gaaggagguu uuccugauag cugcu                                                25

<210> SEQ ID NO 8
<211> LENGTH: 20
<212> TYPE: DNA
<213> ORGANISM: Artificial Sequence
<220> FEATURE:
<223> OTHER INFORMATION: LaminA-C-FWD

<400> SEQUENCE: 8
```
agcaaagtgc gtgaggagtt                                          20

<210> SEQ ID NO 9
<211> LENGTH: 20
<212> TYPE: DNA
<213> ORGANISM: Artificial Sequence
<220> FEATURE:
<223> OTHER INFORMATION: LaminA-C-REV

<400> SEQUENCE: 9
gagttcagca gagcctccag                                          20

<210> SEQ ID NO 10
<211> LENGTH: 22
<212> TYPE: DNA
<213> ORGANISM: Artificial Sequence
<220> FEATURE:
<223> OTHER INFORMATION: GAPDH-FWD

<400> SEQUENCE: 10
catcttccag gagcgagatc cc                                       22

<210> SEQ ID NO 11
<211> LENGTH: 20
<212> TYPE: DNA
<213> ORGANISM: Artificial Sequence
<220> FEATURE:
<223> OTHER INFORMATION: GAPDH-REV

<400> SEQUENCE: 11
ttcacaccca tgacgaacat                                          20

<210> SEQ ID NO 12
<211> LENGTH: 25
<212> TYPE: RNA
<213> ORGANISM: Artificial Sequence
<220> FEATURE:
<223> OTHER INFORMATION: EGFP-N-S

<400> SEQUENCE: 12
gcgccgaggu gaaguucgag ggcga                                    25

<210> SEQ ID NO 13
<211> LENGTH: 27
<212> TYPE: RNA
<213> ORGANISM: Artificial Sequence
<220> FEATURE:
<223> OTHER INFORMATION: EGFP-AS

<400> SEQUENCE: 13
ucgcccucga acuucaccuc ggcgcgg                                  27

<210> SEQ ID NO 14
<211> LENGTH: 25
<212> TYPE: RNA
<213> ORGANISM: Artificial Sequence
<220> FEATURE:
<223> OTHER INFORMATION: EGFP-U-S

<400> SEQUENCE: 14
gcgccgaguu uuaguucgag ggcga                                    25

<210> SEQ ID NO 15
<211> LENGTH: 21
<212> TYPE: RNA
<213> ORGANISM: Artificial Sequence
<220> FEATURE:

```
<223> OTHER INFORMATION: B-GAL-N-S
<220> FEATURE:
<221> NAME/KEY: dTdT
<222> LOCATION: (20)..(21)
<223> OTHER INFORMATION: nn= deoxynucleotides dTdT
<220> FEATURE:
<221> NAME/KEY: misc_feature
<222> LOCATION: (20)..(21)
<223> OTHER INFORMATION: n is dT

<400> SEQUENCE: 15
uuaugccgau cgcgucacan n                                               21

<210> SEQ ID NO 16
<211> LENGTH: 21
<212> TYPE: RNA
<213> ORGANISM: Artificial Sequence
<220> FEATURE:
<223> OTHER INFORMATION: B-GAL-AS
<220> FEATURE:
<221> NAME/KEY: dTdT
<222> LOCATION: (20)..(21)
<223> OTHER INFORMATION: nn= deoxynucleotides dTdT
<220> FEATURE:
<221> NAME/KEY: misc_feature
<222> LOCATION: (20)..(21)
<223> OTHER INFORMATION: n is dT

<400> SEQUENCE: 16
ugugacgcga ucggcauaan n                                               21

<210> SEQ ID NO 17
<211> LENGTH: 21
<212> TYPE: RNA
<213> ORGANISM: Artificial Sequence
<220> FEATURE:
<223> OTHER INFORMATION: B-GAL-U-S
<220> FEATURE:
<221> NAME/KEY: dTdT
<222> LOCATION: (20)..(21)
<223> OTHER INFORMATION: nn= deoxynucleotides dTdT
<220> FEATURE:
<221> NAME/KEY: misc_feature
<222> LOCATION: (20)..(21)
<223> OTHER INFORMATION: n is dT

<400> SEQUENCE: 17
uuaugccguu uucgucacan n                                               21

<210> SEQ ID NO 18
<211> LENGTH: 25
<212> TYPE: RNA
<213> ORGANISM: Artificial Sequence
<220> FEATURE:
<223> OTHER INFORMATION: E7-N-S

<400> SEQUENCE: 18
accggacaga gcccauuaca auauu                                           25

<210> SEQ ID NO 19
<211> LENGTH: 27
<212> TYPE: RNA
<213> ORGANISM: Artificial Sequence
<220> FEATURE:
<223> OTHER INFORMATION: E7-AS

<400> SEQUENCE: 19
aauauuguaa ugggcucugu ccgguuc                                         27

<210> SEQ ID NO 20
```

-continued

```
<211> LENGTH: 25
<212> TYPE: RNA
<213> ORGANISM: Artificial Sequence
<220> FEATURE:
<223> OTHER INFORMATION: E7-U-S

<400> SEQUENCE: 20
accggacauu uuccauuaca auauu                                              25

<210> SEQ ID NO 21
<211> LENGTH: 25
<212> TYPE: RNA
<213> ORGANISM: Artificial Sequence
<220> FEATURE:
<223> OTHER INFORMATION: L12-N-S
<220> FEATURE:
<221> NAME/KEY: dCdT
<222> LOCATION: (24)..(25)
<223> OTHER INFORMATION: mn = deoxyribose nucleotides dCdT
<220> FEATURE:
<221> NAME/KEY: misc_feature
<222> LOCATION: (24)..(25)
<223> OTHER INFORMATION: m is dC, n is dT

<400> SEQUENCE: 21
gcugguccgc cuguccuccg acumn                                              25

<210> SEQ ID NO 22
<211> LENGTH: 27
<212> TYPE: RNA
<213> ORGANISM: Artificial Sequence
<220> FEATURE:
<223> OTHER INFORMATION: L12-AS

<400> SEQUENCE: 22
agagucggag gacaggcgga ccagcuu                                            27

<210> SEQ ID NO 23
<211> LENGTH: 25
<212> TYPE: RNA
<213> ORGANISM: Artificial Sequence
<220> FEATURE:
<223> OTHER INFORMATION: L12-U-S

<400> SEQUENCE: 23
gcugguccuu uuguccuccg acucu                                              25
```